United States Patent [19]

Hillyard et al.

[11] Patent Number: 5,583,003

[45] Date of Patent: Dec. 10, 1996

[54] AGGLUTINATION ASSAY

[75] Inventors: Carmel J. Hillyard; Dennis B. Rylatt, both of Queensland, Australia

[73] Assignee: Agen Limited, Queensland, Australia

[21] Appl. No.: 351,105

[22] Filed: Nov. 30, 1994

Related U.S. Application Data

[63] Continuation of Ser. No. 842,343, filed as PCT/AU90/090453 Sep. 25, 1990, abandoned.

[30] Foreign Application Priority Data

Sep. 25, 1989 [AU] Australia .................... PJ6558

[51] Int. Cl.⁶ .............. G01N 33/53; G01N 33/555; G01N 33/567
[52] U.S. Cl. .............. 435/7.25; 435/7.4; 435/972; 435/973
[58] Field of Search .................... 435/972, 973, 435/7.4, 7.25

[56] References Cited

U.S. PATENT DOCUMENTS

| | | | |
|---|---|---|---|
| 3,639,558 | 2/1972 | Czismas | 424/12 |
| 4,130,634 | 12/1978 | Molinaro | 424/8 |
| 4,200,436 | 4/1980 | Mochida | 23/230 B |
| 4,292,403 | 9/1981 | Duermeyer | 435/5 |
| 4,331,647 | 5/1982 | Goldenberg | 424/1 |
| 4,342,566 | 8/1982 | Theofilopoulos | 23/230 B |
| 4,358,436 | 11/1982 | Graham, Jr. | 424/11 |
| 4,401,764 | 8/1983 | Smith | 436/500 |
| 4,433,059 | 2/1984 | Chang | 436/512 |
| 4,444,878 | 4/1984 | Paulus | 435/7 |
| 4,446,233 | 5/1984 | Auditore-Hargreaves | 435/7 |
| 4,474,893 | 10/1984 | Reading | 436/547 |
| 4,493,793 | 1/1985 | Chu | 260/112 R |
| 4,517,303 | 5/1985 | Freytag | 436/501 |
| 4,550,017 | 10/1985 | Liu | 424/11 |
| 4,578,360 | 3/1986 | Smith | 436/518 |
| 4,607,009 | 8/1986 | Steplewski | 435/7 |
| 4,659,678 | 4/1987 | Forrest | 436/512 |
| 4,661,441 | 4/1987 | Li | 435/7 |
| 4,668,637 | 5/1987 | Guesdon | 436/504 |
| 4,676,980 | 6/1987 | Segal | 424/85 |
| 4,678,747 | 7/1987 | Lloyd | 435/7 |
| 4,683,196 | 7/1987 | McLaughlin | 435/7 |
| 4,695,553 | 9/1987 | Wardlaw | 436/177 |
| 4,745,075 | 5/1988 | Hadfield et al. | 436/523 |
| 4,829,011 | 5/1989 | Gibbons | 436/512 |
| 4,894,347 | 1/1990 | Hillyard et al. | 436/540 |
| 4,900,683 | 2/1990 | Smith, III | 436/519 |
| 5,270,166 | 12/1993 | Parsons et al. | 435/7.4 |

FOREIGN PATENT DOCUMENTS

| | | |
|---|---|---|
| 58-55759 | 4/1983 | Japan . |
| 58-203919 | 11/1983 | Japan . |
| 61-501418 | 7/1986 | Japan . |
| 1-501819 | 6/1989 | Japan . |
| 60113154 | 6/1989 | Japan . |
| WO8303477 | 10/1983 | WIPO . |
| WO8805913 | 8/1988 | WIPO . |

*Primary Examiner*—James C. Housel
*Assistant Examiner*—Ginny Allen Portner
*Attorney, Agent, or Firm*—Iver P. Cooper

[57] ABSTRACT

The assay off the present Invention is of particular use for detecting drugs, hormones, steroids, antibodies and other molecules circulating in the blood of a mammal or other animal.

38 Claims, 10 Drawing Sheets

KEY:

ERYTHROCYTES   CONJUGATES   ANALYTE

AGGLUTINATION ASSAY

This application is a continuation of application Ser. No. 07/842,343, filed Mar. 25, 1992, now abandoned, which is the national stage of PCT/AU90/00453, filed Sep. 25, 1990.

TECHNICAL FIELD

The present invention relates to a reagent and a method for detecting an antigen, antibody or other analyte in a sample, such as human or animal blood, by an agglutination assay. The invention is also directed to a kit containing the reagents and to processes for preparing the reagents.

BACKGROUND OF THE INVENTION

Description of the Background Art

Immunoassays (and analogous specific binding assays) have revolutionized human diagnostic and veterinary medicine since the introduction of techniques such as the radioimmunoassay (RIA), first reported by Yalow and Berson (Nature 184:1648 (1959)), and the enzyme immunoassay (EIA) which was first reported by Engvall and Perlman (Immunochem. 8:871 (1971)) and Van Weeman and Schuurs (FEBS Lett. 15:232 (1971)).

Immunoassays have enabled exquisitely sensitive measurement of analytes circulating in the blood of a subject, and have allowed the determination of levels of hormones, drugs and other compounds present at very low concentrations (such as picomoles/liter). Such assays, based on antibody-antigen interactions, usually involve complex detection systems. The reagents used are generally antigens labeled with an enzyme or a radioisotope, antibodies or complexes thereof which require either incubation with specific substrates and measurement of a color end-point either visually or by means of a colorimeter, or measurement of radioactive decay with radiation counters to detect the presence of the analyte being tested. These assays also involve several washing steps. Most immunoassays for the detection of analytes in blood are currently of this nature. Although these assays are sensitive, they require lengthy and involved procedures and expensive instrumentation.

An alternative to the RIA and EIA is provided by agglutination immunoassays of the type described by Gupta et al., J. Immunol. Meth. 80:177–187 (1985)), wherein erythrocytes and anti-erythrocyte antibodies are used as the indicator system. Typically, foreign erythrocytes, such as sheep erythrocytes, are used in such immunoassays. Both direct and indirect agglutination assays are known in the art. In the conventional direct assay for an antigen, red cells are coated with antibody, and reacted with the sample. Multifunctional antigens act as bridges between the coated red blood cells, creating an agglutinate. In the conventional indirect assay, red cells are coated with antigen, and contacted with both a soluble antibody and with sample. Sample antigen competitively inhibits the binding of sensitized red cells by the antibody, and hence the agglutination.

Agglutination assays may use other agglutinable particles, For example, latex agglutination assays are described in Castelan et al. (J. Clin. Pathol. 21:638 (1968)) and Singer et al. (Amer. J. Med. [1956 (December)]: 888).

Molinaro, U.S. Pat. No. 4,130,634 describes an agglutination assay employing exogenous red blood cells precoated with antibody. The problem of nonspecific agglutination of erythrocytes by anti-erythrocyte antibodies was noted by Czismas, U.S. Pat. No. 3,639,558, who proposed eliminating all naturally occurring antigenic sites on the red blood cell by coating it with protein. Chang, U.S. Pat. No. 4,433,059 precoated exogenous red blood cells with a covalent, "tail-to-tail" conjugate of an anti-erythrocyte antibody (usually univalent) linked by a heterobifunctional coupling agent to an anti-analyte antibody. See also Smith, W088/05931, Gibbons, U.S. Pat. No. 4,329,011 and Smith, III, U.S. Pat. No. 4,900,685. In the method of the latter patent, the agglutinated erythrocytes are endogenous to the sample. Hillyard, Rylatt, Kemp and Bundesen, U.S. Pat. No. 4,894,347 teach an agglutination immunoassay for whole blood samples featuring the use of endogenous erythrocytes as indicator particles, and of an agglutination reagent in which an erythrocyte binding molecule is conjugated to either an analyte-binding molecule (for a direct assay) or to an analyte analogue (for an indirect assay). They discovered that nonspecific agglutination could be avoided, even when the erythrocyte binding molecule was multivalent, if it recognized an abundant, well distributed membrane constituent such as glycophorin.

In U.S. Pat. No, 4,894,347, we pointed out that in an agglutination assay for antigenic analytes large enough to allow simultaneous binding of two antibody molecules, but which lack repeating epitopes, for agglutination to occur, the antigen must interact with the immunoreagent so that at least some molecules of antigen act as a bridge between proximate erythrocytes. We taught that one solution was to employ a reagent comprising two or more distinct conjugates, i.e., ABM1/EBM+ABM2/EBM, where EBM denotes an erythrocyte binding molecule and ABM1 and ABM2 are analyte binding molecules specific for different, non-overlapping, non-repeating epitopes of the analyte. An agglutination assay of this type is depicted in FIG. 1(b).

This solution, however, has a defect which is particularly apparent when analyte concentrations are low, e.g., for HCG less than 10 nM. That is that a molecule of ABM1/EBM and a molecule of ABM2/EBM can bind simultaneously to a single erythrocyte (FIG. 1(c)). The bound analyte molecule then does not act as a bridge between proximate erythrocytes and therefore does not promote agglutination. Smith, U.S. Pat. No. 4,578,360 and Smith, U.S. Pat. No. 4,401,764 describe conjugates of an erythrocyte binding molecule and a label binding molecule. Chu, U.S. Pat. No. 4,493,793 constructed covalently coupled lectin-antibody or lectin-antigen conjugates. Segal, U.S. Pat. No. 4,676,980 prepared an antibody-antibody immuno therapeutic conjugate for associating a target (e.g., tumor) cell with a cytotoxic effector cell. Freytag, U.S. Pat. No. 4,517,303 describes an immunolytic assay employing a conjugate between an analyte analogue and a cytolysin, e.g., whole mellitin. Li, U.S. Pat. No. 4,661,441 referred to a conjugate of an analyte-binding antibody and an antibody specific for the idiotype of the analyte-binding moiety.

Wardlaw, U.S. Pat. No. 4,695,553 and Guesdon, U.S. Pat. No. 4,668,637 relate to use of "universal" anti-erythrocyte antibodies (and cf. McLaughlin, U.S. Pat. No. 4,683,196), while type-specific antibodies are taught by Lloyd, U.S. Pat. No. 4,678,747, Graham Jr., U.S. Pat. No. 4,358,436, Lu, U.S. Pat. No. 4,550,017, Steplewski, U.S. Pat. No. 4,607,009 and Lennox, W083/03477. Bigtee, Molec. Immunol., 20:1353–1362 (1983) describes the production and testing of anti-glycophorin monoclonal antibodies; Wardlaw suggested use of an anti-glycophorin antibody in clarifying the interface between erythrocytes and leukocytes in centrifuged whole blood. This group of references does not disclose conjugating the erythrocyte binding molecule "tail-to-tail" to another binding molecule.

It is known in the art that a blood sample may be divided into a plurality of aliquots which are then assayed separately for the presence of different analytes. We are not aware of any reference which teaches or suggests dividing a blood sample, reacting the aliquots with different agglutination reagents, and then recombining the sample to obtain increased sensitivity to a single analyte.

Theofilopoulos (U.S. Pat. No. 4,342,566), Duermeyer (U.S. Pat. No. 4,292,403) and Goldenberg (U.S. Pat. No. 4,331,647) demonstrate the use of antigen binding fragments of antibodies as substitutes for intact antibodies in immunological assays. The construction of heterobifunctional antibodies is taught by Auditore-Hargreaves (U.S. Pat. No. 4,446,233), Paulus (U.S. Pat. No. 4,444,878) and Reading (U.S. Pat. No. 4,474,893). Mochida (U.S. Pat. No. 4,200,436) discloses the use of monovalent antibodies, or antigen-binding fragments thereof, in certain immunoassays. Forrest (U.S. Pat. No. 4,659,678) mentions that monovalent antibodies cannot form dimers or more extensive complexes with the antigen; such monovalent antibody-antigen aggregates were said to be capable of interfering with the binding of the antigen-antibody complex to a solid phase support.

Traditional hemagglutination assays are generally faster, but less sensitive than radioimmunoassays (RIA) or enzyme immunoassays (EIA). The speed and sensitivity of hemagglutination assays can be increased by the use of the autologous red cell agglutination technique described in, e.g., U.S. Pat. No. 4,894,347. The advantage of such a technique is that blood does not have to be separated; a single finger prick is sufficient to provide an assayable sample. For analytes which are large molecules with repeating epitopes, the sensitivity of such an assay is sufficient.

The present inventors recognized a need in the art for improved sensitivity in autologous agglutination assays, in particular for detection of hormones such as human chorionic gonadotrophin (HCG) in the early stages of pregnancy. Such assays with increased sensitivity could also serve as alternatives to inhibition assays in the immunodetection of small molecules. Inhibition assays are inherently less sensitive than direct assays, and the end point is more difficult to define.

No admission is made that any reference cited in this specification is prior art. All references are hereby incorporated by reference.

SUMMARY OF THE INVENTION

It is the object of the present invention to overcome the deficiencies of the art set forth above. The invention is useful in assaying low concentrations of antigens lacking repeating determinants. We provide a method by which these analytes may be assayed directly. In particular, we describe herein a direct agglutination assay wherein an analyte which has two nonrepeating epitopes may be detected without loss of sensitivity due to the formation of multiple "bridges" between an analyte molecule and a single agglutinable particle.

According to a first embodiment of this invention there is provided a direct agglutination assay for the detection of an analyte in a sample, wherein the analyte includes a first nonrepeating epitope and a second nonrepeating epitope, the assay comprising:

(a) providing first and second primary agglutination reagents, each of which is capable of binding simultaneously to an agglutinable particle, and to a nonrepeating epitope of said analyte, said first and second reagents binding to different, non-overlapping epitopes of said analyte;

(b) forming a first mixture of a first sample portion, said first reagent, and agglutinable particles bindable by said first reagent;

(c) forming a second mixture of a second sample portion, said second reagent, and agglutinable particles bindable by said second reagent; and (d) forming a third mixture by mixing said first and second mixtures, wherein agglutination in the third mixture indicates the presence of the analyte in the sample.

According to a second embodiment of this invention there is provided a direct agglutination assay for the detection of an analyte in a sample, wherein the analyte includes a first binding site, the assay comprising:

(a) providing a first primary agglutination reagent which is capable of binding to an agglutinable particle and to said analyte epitope, and which when bound to said analyte epitope forms a second epitope;

(b) forming a first mixture of a first sample portion, said first reagent, and agglutinable particles bindable by said first reagent;

(c) providing a second primary agglutination reagent which is capable of binding to an agglutinable particle and to said second epitope;

(d) forming a second mixture of a second sample portion, said second reagent, and agglutinable particles bindable by the second reagent, said second epitope being bindable by said second reagent; and (e) forming a third mixture by mixing said first and second mixtures, wherein agglutination in the third mixture indicates the presence of the analyte in the sample.

According to a third embodiment of this invention there is provided a two site direct agglutination assay for the detection of the simultaneous presence of two different analytes in a sample wherein the first and second analytes each comprise at least one analyte-binding site, the assay comprising:

(a) providing a first primary agglutination reagent which is capable of binding simultaneously to an agglutinable particle and to said first analyte;

(b) providing a second primary agglutination reagent which is capable of binding simultaneously to the same or a different type of epitope of an agglutinable particle and to said second analyte;

(c) providing agglutinable particles to which said first and second primary agglutination reagents can bind, if such particles are not already present in the sample;

(d) forming a first mixture of a first sample portion, said first agglutination reagent, and bindable agglutinable particles to obtain first analyte:first agglutination reagent:particle complex;

(e) forming a second mixture of a second sample portion, second primary agglutination reagent, and bindable agglutinable particles to obtain second analyte:second reagent:particle complex;

(f) providing a secondary agglutination reagent which can bind simultaneously to both said first complex and to said second complex, in each case being specific for either a native epitope of the analyte or an epitope formed by the binding of the primary reagent to said analyte, but not able to bind to two complexes of the same analyte;

(g) forming a third mixture of said first and second mixtures and said secondary agglutination reagents.

wherein agglutination of said third mixture indicates the simultaneous presence of said first and second analytes in the sample.

According to a fourth embodiment of this invention there is provided a direct agglutination assay for the detection of an analyte in a sample, wherein the analyte includes a first nonrepeating epitope and a second nonrepeating epitope, the assay comprising:

(a) providing a first primary agglutination reagent which is capable of binding simultaneously to an agglutinable particle, and to a nonrepeating epitope of said analyte;

(b) forming a first mixture of a first sample portion, said first reagent, and agglutinable particles bindable by said first reagent;

(c) providing a primary agglutination agent comprising a second primary agglutination reagent:agglutinable particle complex wherein said second primary agglutination reagent is capable of binding to a nonrepeating epitope of said analyte and said first and second reagents binding to different, non-overlapping epitopes of said analyte;

(d) forming a second mixture of said first mixture and said agent, and agglutinable particles bindable by said first reagent;

wherein agglutination in the second mixture indicates the presence of the analyte in the sample.

According to a fifth embodiment of this invention there is provided a direct agglutination assay for the detection of an analyte in a sample, wherein the analyte includes a first binding site, the assay comprising:

(a) providing a first primary agglutination reagent which is capable of binding to an agglutinable particle and to said analyte epitope, and which when bound to said analyte epitope forms a second epitope;

(b) forming a first mixture of a first sample portion, said first reagent, and agglutinable particles bindable by said first reagent;

(c) providing a primary agglutination agent comprising a second primary agglutination reagent:agglutinable particle complex wherein said second primary agglutination reagent is capable of binding to said second epitope; and (d) forming a second mixture by mixing said first mixture and said agent wherein agglutination in the second mixture indicates the presence of the analyte in the sample.

According to a sixth embodiment of this invention there is provided a two site direct agglutination assay for the detection of the simultaneous presence of two different analytes in a sample wherein the first and second analytes each comprise at least one analyte-binding site, the assay comprising:

(a) providing a first primary agglutination reagent which is capable of binding simultaneously to an agglutinable particle and to said first analyte;

(b) providing agglutinable particles to which said first primary agglutination reagent can bind, if such particles are not already present in the sample;

(c) forming a first mixture of a first sample portion, said first agglutination reagent, and bindable agglutinable particles to obtain first analyte:first agglutination reagent:particle complex;

(d) providing a primary agglutination agent comprising a second primary agglutination reagent:particle complex wherein said second primary agglutination reagent is capable of binding to said second analyte thereby forming a second complex;

(e) providing a secondary agglutination reagent which can bind simultaneously to both said first complex and to said second complex, in each case being specific for a native epitope of the analyte or an epitope formed by the binding of the primary reagent to said analyte, but not able to bind to two complexes of the same analyte;

(f) forming a second mixture of said first mixture, said primary agglutination agent and said secondary agglutination reagents, wherein agglutination of said second mixture indicates the simultaneous presence of said first and second analytes in the sample.

According to a seventh embodiment of this invention there is provided a two site direct agglutination assay for the detection of the simultaneous presence of two different analytes in a sample wherein the first and second analytes each comprise at least one analyte-binding site, the assay comprising:

(a) providing a first primary agglutination agent comprising a first primary agglutination reagent:particle complex wherein said first primary agglutination reagent is capable of binding to said first analyte thereby forming a first complex;

(b) providing a second primary agglutination agent comprising a second primary agglutination reagent:particle complex wherein said second primary agglutination reagent is capable of binding to said second analyte thereby forming a second complex;

(e) providing a secondary agglutination reagent which can bind simultaneously to both said first complex and to said second complex, in each case being specific for a native epitope of the analyte or an epitope formed by the binding of the primary reagent to said analyte, but not able to bind to two complexes of the same analyte;

(f) forming a first mixture of said sample, said first and second primary agglutination agents and said secondary agglutination reagents, wherein agglutination of said first mixture indicates the simultaneous presence of said first and second analytes in the sample.

According to an eighth embodiment of this invention there is provided a two site direct agglutination assay for the detection of the simultaneous presence of three different analytes in a sample wherein each of said analytes comprise at least one analyte binding site, the assay comprising:

(a) providing a first primary agglutination reagent which is capable of binding simultaneously to a first agglutinable particle and to a first analyte;

(b) providing a second primary agglutination reagent which is capable of binding simultaneously to a second agglutinable particle and to a second analyte;

(c) providing first and second agglutinable particles to which said said first and secondary primary agglutination reagents can bind respectively, if such particles are not already present in said sample;

(d) forming a first mixture of a first portion of the sample, said first primary agglutination reagent and said first agglutinable particles to obtain a first analyte:first primary agglutination reagent:first particle complex;

(e) forming a second mixture of a second portion of the sample, said second primary agglutination reagent and said second agglutinable particles to obtain a second analyte:second primary agglutination reagent:second particle complex;

(f) providing first and second secondary agglutination reagents wherein said first secondary agglutination reagents can bind simultaneously to both said first complex and to a third analyte, and said second secondary agglutination reagent can bind simultaneously to both said second complex and to said third analyte;

(g) forming a third mixture of the first mixture, the second mixture and the first and second secondary agglutination reagents, wherein agglutination of said third mixture indicates the simultaneous presence of said first, second and third analytes in the sample.

According to a ninth embodiment of this invention there is provided a two site direct agglutination assay for the detection of the simultaneous presence of a plurality of different analytes in a sample wherein each of said analytes comprise at least one analyte binding site, the assay comprising:

(a) providing a first primary agglutination reagent which is capable of binding simultaneously to a first agglutinable particle and to a first analyte;

(b) providing a second primary agglutination reagent which is capable of binding simultaneously to a second agglutinable particle and to a second analyte;

(c) providing first and second agglutinable particles to which said said first and secondary primary agglutination reagents can bind respectively, if such particles are not already present in said sample;

(d) forming a first mixture of a first portion of the sample, said first primary agglutination reagent and said first agglutinable particles to obtain a first analyte:first primary agglutination reagent:first particle complex;

(e) forming a second mixture of a second portion of the sample, said second primary agglutination reagent and said second agglutinable particles to obtain a second analyte:second primary agglutination reagent:second particle complex;

(f) providing first and second secondary agglutination reagents wherein said first secondary agglutination reagent can bind simultaneously to both said first complex and to a third analyte, and said second secondary agglutination reagent can bind simultaneously to both said second complex and to a fourth analyte;

(g) providing (n+1)th tertiary agglutination reagents which can bind simultaneously with two different of (n)th additional analytes wherein a first tertiary agglutination reagent binds to said third analyte and a first additional analyte and a second tertiary agglutination reagent binds to said fourth analyte and a second additional analyte and wherein n is an integer of 2 or more;

(h) forming a third mixture of said first and second mixtures, said first and second agglutinable particles, and said (n+1)th tertiary agglutination reagents, wherein agglutination of said third mixture indicates the simultaneous presence of said plurality of different analytes in said sample. 'n' is typically from 2 to 100.

According to a tenth embodiment of this invention there is provided an agglutination assay for the detection of an analyte in a particulate-containing sample wherein the analyte comprises at least three binding sites, the assay comprising:

mixing a first conjugate comprising a particulate-binding molecule and an analyte binding molecule capable of binding to first and second binding sites on the analyte with a first particulate-containing sample to form a first mixed sample, mixing a second conjugate comprising a particulate-binding molecule and an analyte binding molecule capable of binding to a third binding site on the analyte with a second particulate-containing sample to form a second mixed sample, mixing the first mixed sample with the second mixed sample wherein agglutination of the combined mixed samples indicates presence of analyte in the first particulate-containing sample.

According to an eleventh embodiment of this invention there is provided an assay for an allergen-specific IgE antibody in whole blood comprising:

(a) providing a heterobispecific anti-erythrocyte and anti-IgE antibody specific for the IgE of the species from which said whole blood is obtained, said heterobispecific antibody being capable of binding to only one site on the IgE molecule;

(b) providing a known quantity of a multivalent allergen bound by said IgE antibody;

(c) reacting the whole blood sample with said heterobispecific antibody and said allergen, whereby erythrocytes endogenous to said whole blood sample are agglutinated if and only if an IgE antibody which binds said allergen multivalently is present.

According to a twelfth embodiment of this invention there is provided an assay for an allergen-specific IgM antibody in whole blood comprising:

(a) providing a heterobispecific anti-erythrocyte and anti-IgM antibody specific for the IgM of the species from which said whole blood is obtained, said heterobispecific antibody being capable of binding to only one site on the IgM molecule;

(b) providing a known quantity of a multivalent allergen bound by said IgM antibody;

(c) reacting the whole blood sample with said heterobispecific antibody and said allergen whereby erythrocytes endogenous to said whole blood sample are agglutinated if and only if an IgM antibody which binds said allergen multivalently is present.

Generally, mixing of the first conjugate with the first sample and the second conjugate with the second sample are typically done over 1–2 minutes. The first mixed sample and the second mixed sample are typically mixed together for 1–2 minutes. A strong positive will agglutinate in 10–20 seconds.

In one embodiment, the sample is divided into two portions. A first primary agglutination reagent (R1) which can simultaneously bind both an agglutinable indicator particle and a first, nonrepeating epitope analyte of interest is combined with the analyte in the first portion and with indicator particle (which may be endogenous or exogenous to the sample). A second primary agglutination reagent (R2), similar in function except that it binds a second, nonrepeating epitope of the analyte, is combined with the second portion and with indicator particle. The stoichiometry of the reaction is such that there is essentially no uncomplexed analyte in either portion. Also, essentially all the excess reagent is particle bound (P-R1 or P-R2).

The two sample portions are now recombined. The Particle-Reagent1-Analyte complex which has a free second epitope, reacts with the Reagent2-Particle (P-R2) complex. The Particle-Reagent2-Analyte complex which has a free first epitope, reacts with the Reagent1-Particle (P-R1) complex. Each reagent molecule is already bound to one particle (from one portion), but is free to bind only to an analyte molecule complexed to another particle (from the other portion). Multiple bridges between a single particle and a single analyte molecule are avoided.

In a second embodiment, the assay is adapted to the situation where the analyte initially has only a single, nonrepeating epitope. It relies on the fact that the immune complex of the first reagent and the analyte has epitopes which are not found on either the reagent or the analyte alone. The second reagent binds to such a formed epitope, rather than to an epitope native to the analyte.

In a third embodiment, we also employ a third, bispecific secondary agglutination reagent which conjugates a first complex comprising analyte (from the first sample portion) bound to a particle through the first reagent, and a second complex comprising analyte (from the second sample portion) bound to a particle through the second reagent. Each valency of the third reagent may be for either a native epitope of the analyte or one formed by the analyte-R1 or analyte-R2 complex.

If the specificities of the third reagent are chosen so that it is incapable of conjugating first complex-to-first complex or second complex-to-second complex, it will not be able to conjugate two analyte molecules conjugated already to the same particle, and therefore, will more efficiently contribute to the formation of the desired agglutinate.

According to a thirteenth embodiment of this invention there is provided a test kit for use in a direct agglutination assay, for the detection of an analyte in a particulate-containing sample, which comprises:

(a) a first conjugate comprising a particulate-binding molecule and a first analyte binding molecule capable of binding to a first binding site on the analyte, and (b) a second conjugate comprising a particulate-binding molecule and a second analyte binding molecule capable of binding to a second binding site of the analyte.

According to a fourteenth embodiment of this invention there is provided a test kit for use in a direct agglutination assay for the detection of an analyte in a particulate-containing sample, comprising a single binding site, which comprises:

(a) a first conjugate comprising a particulate-binding molecule and a first analyte binding molecule capable of binding to the single binding site of the analyte, and (b) a second conjugate comprising a particulate-binding molecule and a second analyte binding molecule capable of binding to the first analyte binding molecule bound to the analyte.

According to a fifteenth embodiment of this invention there is provided a test kit for use in a two site direct agglutination assay for the detection of an analyte in a particulate-containing sample, wherein the analyte comprises at least two binding sites, which comprises:

(a) a first conjugate comprising a particulate-binding molecule and a first analyte binding molecule capable of binding to a first binding site on the analyte, (b) a second conjugate comprising a particulate-binding molecule and a second analyte binding molecule capable of binding to a second binding site of the analyte, and (c) a crosslinking reagent which comprises a dimeric analyte binding molecule capable of binding to a third binding site on the analyte.

According to a sixteenth embodiment of this invention there is provided a test kit for use in a two site direct agglutination assay for the detection of an analyte in a particulate-containing sample, wherein the analyte comprises at least two binding sites, which comprises:

(a) a first conjugate comprising a particulate-binding molecule and a first analyte binding molecule capable of binding to a first binding site on the analyte, (b) a second conjugate comprising a particulate-binding molecule and a second analyte binding molecule capable of binding to a second binding site on the analyte, and (c) a crosslinking reagent which comprises a divalent hybrid analyte binding molecule capable of binding to third and fourth binding sites on the analyte.

According to a seventeenth embodiment of this invention there is provided a test kit for use in a two site direct agglutination assay for the detection of an analyte in a particulate-containing sample, wherein the analyte comprises at least two binding sites, which comprises:

(a) a first conjugate comprising a particulate-binding molecule and a first analyte binding molecule capable of binding to a first binding site on the analyte, (b) a second conjugate comprising a particulate-binding molecule and a second analyte binding molecule capable of binding to a second binding site on the analyte, and (c) a crosslinking reagent which comprises a divalent hybrid analyte binding molecule capable of binding to a third binding site on the analyte and to a site generated by the binding of the first analyte binding molecule or the second analyte binding molecule to the analyte.

According to an eighteenth embodiment of this invention there is provided a test kit for use in a two site direct agglutination assay for the detection of an analyte in a particulate-containing sample, wherein the analyte comprises at least two binding sites, which comprises:

(a) a first conjugate comprising a particulate-binding molecule and a first analyte binding molecule capable of binding to a first binding site on the analyte, (b) a second conjugate comprising a particulate-binding molecule and a second analyte binding molecule capable of binding to a second binding site on the analyte, and 6

(c) a crosslinking reagent which comprises a divalent hybrid analyte binding molecule which is capable of binding to a site generated by the binding of the first analyte binding molecule and to a site generated by the binding of the second analyte binding molecule to the analyte.

According to a nineteenth embodiment of this invention there is provided a test kit for use in a two site direct agglutination assay for the detection of an analyte in a particulate-containing sample wherein the analyte comprises at least two binding sites, which comprises:

(a) a first conjugate comprising a particulate-binding molecule and a first analyte binding molecule capable of binding to a first binding site on the analyte, (b) a second conjugate comprising a particulate-binding molecule and a second analyte binding molecule capable of binding to a second binding site on the analyte, and (c) a crosslinking reagent which comprises a divalent hybrid analyte binding molecule capable of binding to the first binding site on the analyte and to the second binding site on the analyte.

According to a twentieth embodiment of this invention there is provided a test kit for use in a two site direct agglutination assay for the detection of an analyte in a particulate-containing sample wherein the analyte comprises at least two binding sites, which comprises:

(a) a first conjugate comprising a particulate-binding molecule and a first analyte binding molecule which binds to a first binding site on the analyte, (b) a second conjugate comprising a particulate-binding molecule and a second analyte binding molecule capable of binding to a second binding site on the analyte, and (c) a crosslinking reagent comprising a divalent hybrid analyte binding molecule capable of binding to the second binding site on the analyte and to a site generated by the binding of the second analyte binding molecule to the second binding site.

According to a twenty first embodiment of this invention there is provided a test kit for use in a two site direct agglutination assay for the simultaneous detection of two different analytes in a particulate-containing sample, wherein the first and second analytes each comprise at least one analyte binding site, which comprises:

(a) a first conjugate comprising a particulate-binding molecule and a first analyte binding molecule capable of binding to a first binding site on the first analyte, (b) a second conjugate comprising a particulate-binding molecule and a second analyte binding molecule capable of binding to a second binding site on the second analyte, and (c) a crosslinking reagent which comprises a dimeric analyte binding molecule capable of binding to a third binding site on the first analyte and to a fourth binding site on the second analyte.

According to a twenty second embodiment of this invention there is provided a test kit for use in a two site direct agglutination assay for the simultaneous detection of two different analytes in a particulate-containing sample, wherein the first and second analytes each comprise at least one analyte binding site, which comprises:

(a) a first conjugate comprising an erthrocyte binding molecule and a first analyte binding molecule capable of binding to a first binding site on the first analyte, (b) a second conjugate comprising an erthrocyte binding molecule and a second analyte binding molecule capable of binding to a second binding site on the second analyte, and (c) a crosslinking reagent which comprises a divalent hybrid analyte binding molecule capable of binding to a third binding site on the first analyte and to a fourth binding site on the second analyte generated by the binding of the second analyte binding molecule to the second analyte.

According to a twenty third embodiment of this invention there is provided a test kit for use in a two site direct agglutination assay for the simultaneous detection of two different analytes in a particulate-containing sample, wherein the first and second analytes each comprise at least one analyte binding site, which comprises:

(a) a first conjugate comprising a particulate-binding molecule and a first analyte binding molecule capable of binding to a first binding site on the first analyte molecule, (b) a second conjugate comprising a particulate-binding molecule and a second analyte binding molecule capable of binding to a second binding site on the second analyte, and (c) a crosslinking reagent which comprises a divalent hybrid analyte binding molecule capable of binding to a third binding site on the first analyte generated by the binding of the first analyte binding molecule to the first analyte and to a fourth binding site on the second analyte generated by the binding of the second analyte binding molecule to the second analyte.

According to a twenty fourth embodiment of this invention there is provided a test kit for use in a two site direct agglutination assay for the simultaneous detection of two different analytes in a particulate-containing sample, wherein the first and second analytes each comprise at least one analyte binding site, which comprises:

(a) a first conjugate comprising a particulate-binding molecule and a first analyte binding molecule capable of binding to a first binding site on the first analyte, (b) a second conjugate comprising a particulate-binding molecule and a second analyte binding molecule capable of binding to a second binding site on the second analyte, and (c) a crosslinking reagent which comprises a divalent analyte binding molecule capable of binding to a third binding site present on each of the first and second analytes.

According to a twenty fifth embodiment of this invention there is provided a test kit for an agglutination assay for the detection of an analyte in a particulate-containing sample wherein the analyte comprises at least three binding sites, comprising:

(a) a first conjugate comprising a particulate-binding molecule and an analyte binding molecule capable of binding to first and second binding sites on the analyte; and (b) a second conjugate comprising a particulate-binding molecule and an analyte binding molecule capable of binding to a third binding site on the analyte.

According to a twenty sixth embodiment of this invention there is provided a test kit for use in a direct agglutination assay for the detection of an analyte in a first particulate-containing sample, wherein the analyte comprises a first binding site and a second binding site, which comprises:

(a) a first conjugate comprising a first particulate binding molecule and an analyte binding molecule capable of binding to the first binding site; and (b) a reagent prepared by mixing/reacting a second particulate-containing sample with a second conjugate comprising an analyte binding molecule capable of binding to the second binding site and a second particulate binding molecule.

According to a twenty seventh embodiment of this invention there is provided a test kit for a direct agglutination assay for the detection of an analyte in a first particulate-containing sample, wherein the analyte comprises a binding site, which comprises:

(a) a first conjugate comprising a first particulate-binding molecule and an analyte binding molecule capable of binding to the binding site, and thereby forms a second binding site; and (b) a reagent prepared by mixing/reacting a second particulate-containing sample with a second conjugate comprising an analyte binding molecule capable of binding to the second binding site and a second particulate binding molecule.

According to a twenty eighth embodiment of this invention there is provided a test kit for a two site direct agglutination assay for the detection of an analyte in a first particulate-containing sample, wherein the analyte comprises at least two binding sites, which comprises:

(a) a first conjugate comprising a first particulate-binding molecule and an analyte binding molecule capable of binding to a first binding site on the analyte;

(b) a reagent prepared by mixing/reacting a second particulate-containing sample with a second conjugate comprising an analyte binding molecule capable of binding to the second binding site and a second particulate binding molecule; and (c) a crosslinking reagent.

In one form the cross linking reagent comprises a dimeric analyte binding molecule capable of binding to a third analyte binding site on the analyte.

In another form the crosslinking reagent comprises a divalent hybrid analyte binding molecule capable of binding to a third analyte binding site on the analyte and on a fourth analyte binding site on the analyte.

In a further form the crosslinking reagent comprises a divalent hybrid divalent analyte binding molecule capable of binding to a third analyte binding site on the analyte and to a site generated by the binding of the first analyte binding molecule to the first binding site or the second analyte binding molecule to the second binding site.

In yet another form the crosslinking reagent comprises a divalent hybrid analyte binding molecule capable of binding to a site generated by the binding of the analyte binding molecule to the first binding site, and to a site generated by the binding of the second analyte binding molecule to the second binding site.

In yet a further form the crosslinking reagent comprises a divalent hybrid analyte binding molecule capable of binding to the first binding site in the analyte and to the second binding site on the analyte.

In another form the crosslinking reagent comprises a divalent hybrid analyte binding molecule capable of binding to the second binding site on the analyte and to a site generated by the binding of the second analyte binding molecule to the second binding site.

According to a twenty ninth embodiment of this invention there is provided a test kit for a two site direct agglutination assay for the simultaneous detection of two different analytes in a first particulate-containing sample wherein the first and second analytes each comprise at least one analyte binding site, which comprises:

(a) a first conjugate comprising a first particulate-binding molecule and a first analyte binding molecule capable of binding to a first analyte binding site on the first analyte;

(b) a reagent prepared by mixing/reacting a second particulate-containing sample with a second conjugate comprising an analyte binding molecule capable of binding to the second binding site and a second particulate binding molecule; and (c) a crosslinking reagent.

In one form the crosslinking reagent comprises a divalent hybrid analyte binding molecule capable of binding to a third analyte binding site on the first analyte and a fourth analyte binding site on the second analyte.

In another form, the crosslinking reagent comprises a divalent hybrid analyte binding molecule capable of binding to a third analyte binding site on the first analyte and to a fourth analyte binding site generated by the binding of the second analyte binding molecule to the second analyte.

In yet another form, the crosslinking reagent comprises a divalent hybrid analyte binding molecule capable of binding to a third analyte binding site generated by the binding of the first analyte binding molecule to the first analyte, and to a fourth analyte binding site generated by the binding of the second analyte binding molecule to the second analyte.

In a further form, the crosslinking reagent comprises a divalent analyte binding molecule capable of binding to a third analyte binding site present on each of the first and second analytes.

According to a thirtieth embodiment of this invention there is provided test kit for an agglutination assay for the detection of an analyte in a first particulate-containing sample wherein the analyte comprises at least three binding sites, which comprises:

(a) a first conjugate comprising a first particulate-binding molecule and an analyte binding molecule capable of binding to first and second binding sites on the analyte; and (b) a reagent prepared by mixing/reacting a second particulate-containing sample with a second conjugate comprising an analyte binding molecule capable of binding to a third binding site on the analyte and a particulate-binding molecule.

Generally, in the twenty sixth to thirtieth embodiments the particles in the second particulate-containing sample are different from the particles in the first particulate-containing sample. Generally, the particulate-containing samples can be whole blood, semen, culture of hybridoma cells, samples obtained from microbial fermentation and tissue culture, for example. Alternatively, the particulate-containing samples can contain synthetic or artificial particles such as carbohydrates, latex (natural or synthetic rubber or plastic), glass beads, carbohydrates (cellulose) liposomes and metal oxide particles, for example.

BRIEF DESCRIPTION OF THE DRAWINGS

FIG. 9 represents the assay for allergen-specific IgE. The conjugate consists of a bi-specific anti-erythrocyte-anti IgE antibody which binds to only one site on the IgE. The allergen is added as a multivalent moiety, either alone or bound to a carrier such as latex or a protein. Agglutination occurs when IgE antibodies, specific to the allergen are present in the sample.

FIG. 10 represents the assay for specific IgM. The conjugate consists of a bi-specific anti erythrocyte-anti IgM antibody which binds to only one site on the IgM. The antigen is added as a multivalent moiety, either alone or bound to a carrier such as latex or a protein. Agglutination occurs when IgM antibodies, specific to the antigen are present in the sample.

BEST MODE AND OTHER MODES FOR CARRYING OUT THE INVENTION

Figure 1A:
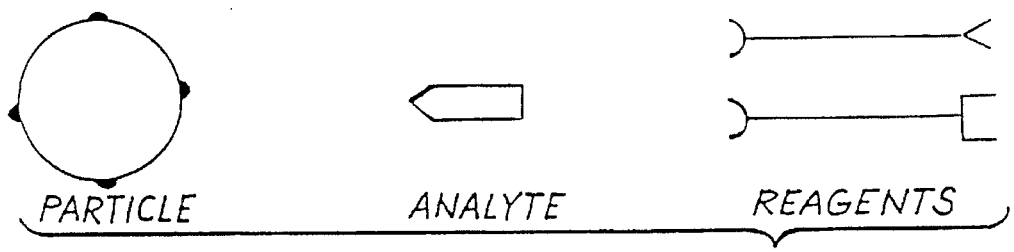
FIG. 1(a) shows the three components of an agglutination assay described in the Hillyard patent: a particle with multiple epitopes, an analyte with two different nonrepeating epitopes, and two primary agglutination reagents, both of which bind the particle, but which also bind the analyte at the different epitopes.
Figure 1B:
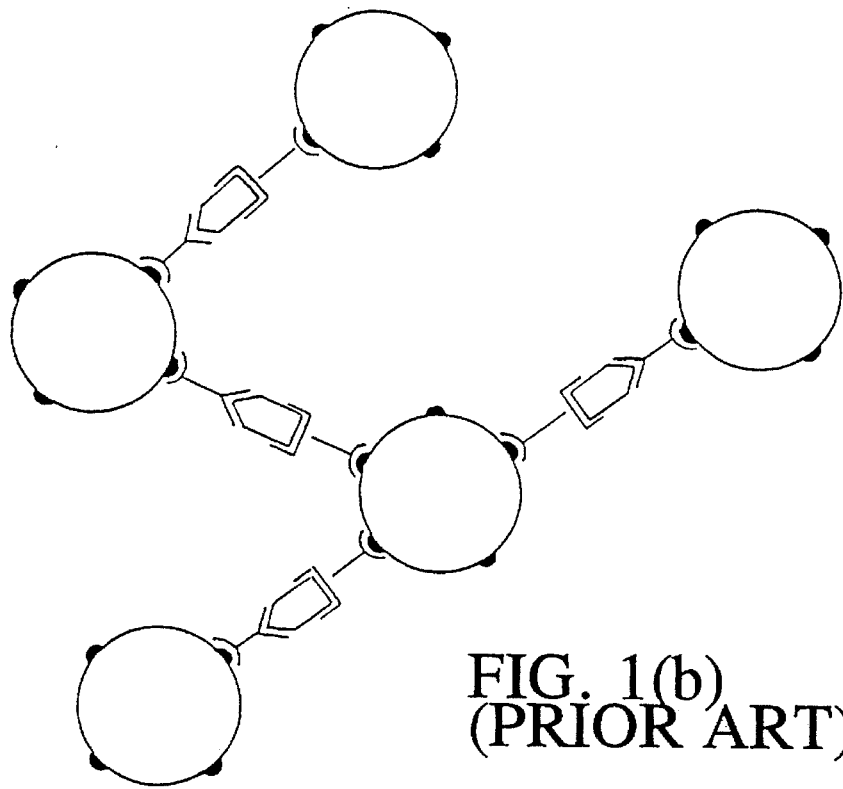
FIG. 1(b) shows an agglutinate formed by the sequential or simultaneous combination of the aforementioned reaction components.
Figure 1C:
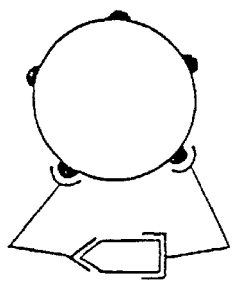
FIG. 1(c) reveals how sensitivity can be reduced through the formation of multiple bridges between one molecule of analyte and one erythrocyte.
Figure 2:
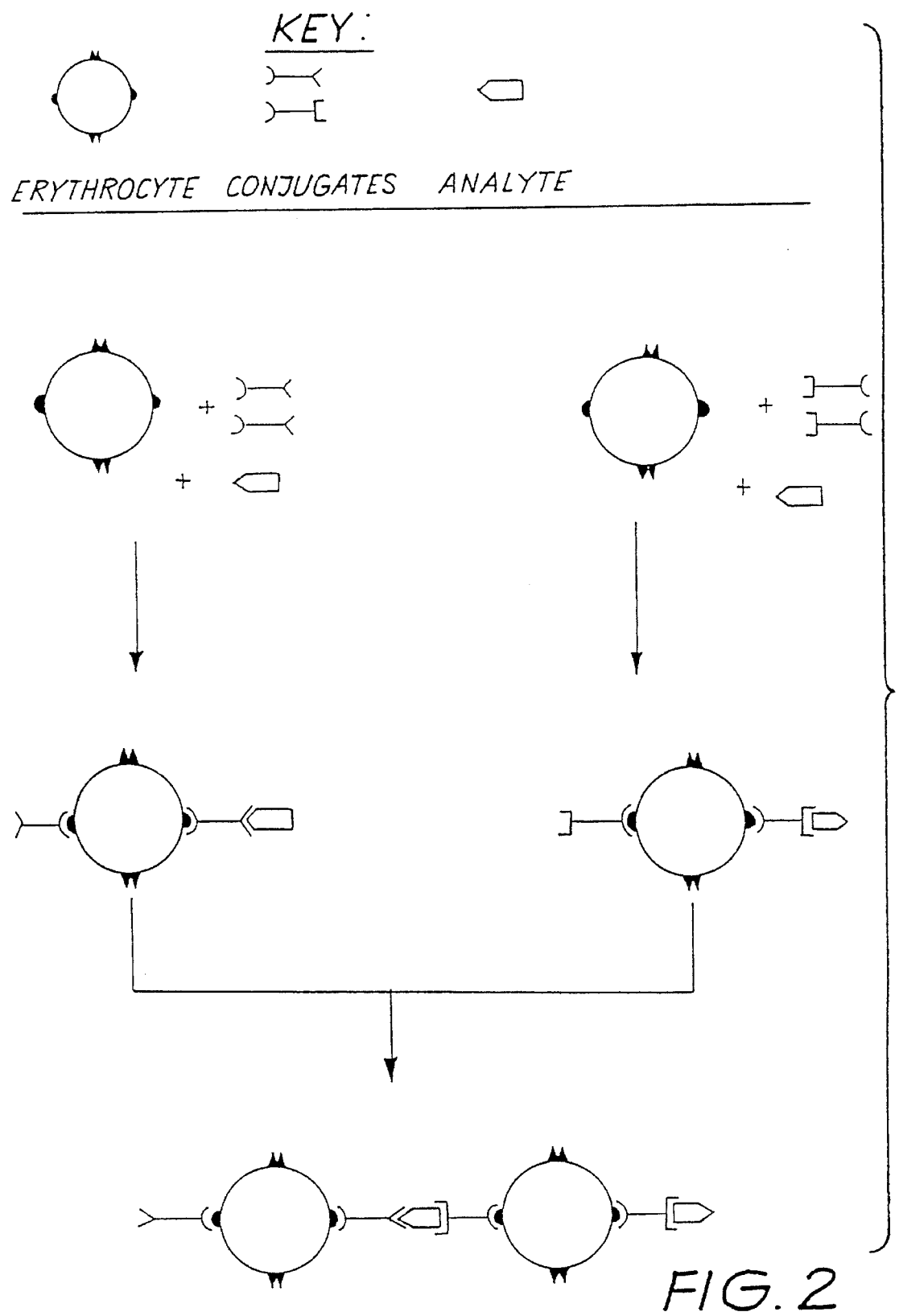
FIG. 2 illustrates the present invention. The sample is divided into two portions, each of which is reacted with particles and with one or the other of the two primary agglutination reagents. When the two portions are recombined, only "interparticle" bridges can form.
Figure 3:
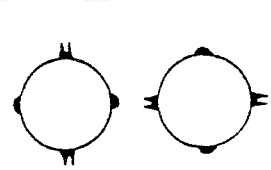
FIG. 3 depicts a variant on the above in which the analyte need only have a single, nonrepeating epitope. In the reaction shown on the left side, the binding of the first reagent to the analyte creates a new epitope which is recognized by the second reagent shown on the right side when the sample portions are recombined.
Figure 3:
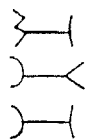
Figure 3:
Figure 3:
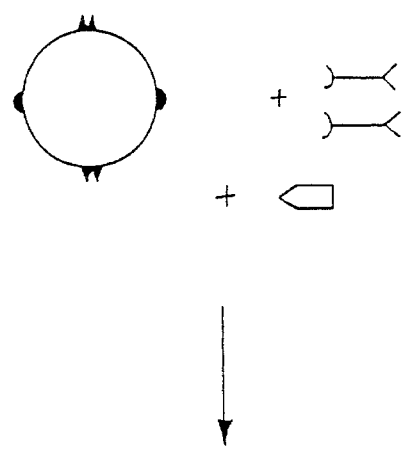
Figure 3:
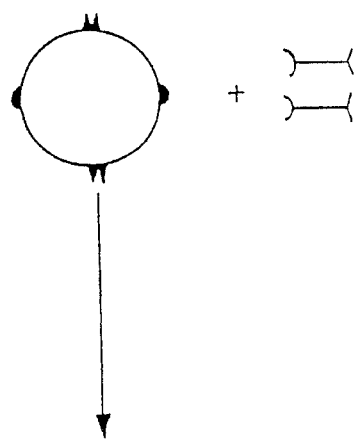
Figure 3:
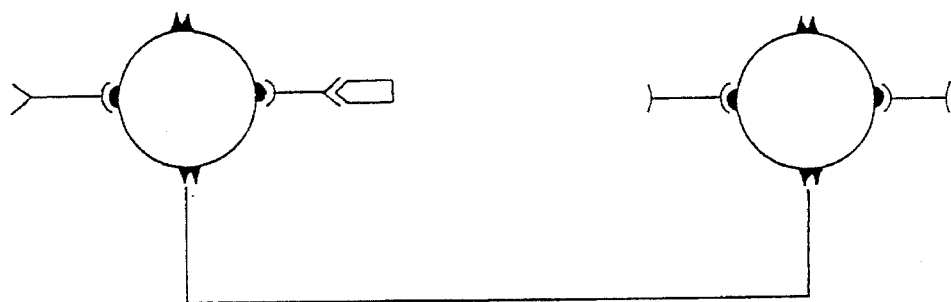
Figure 3:
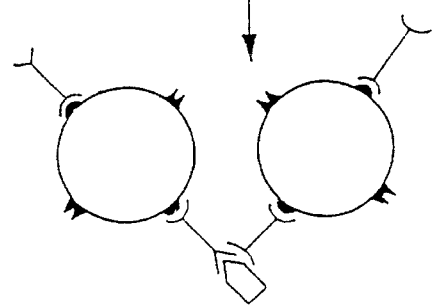
Figure 4:
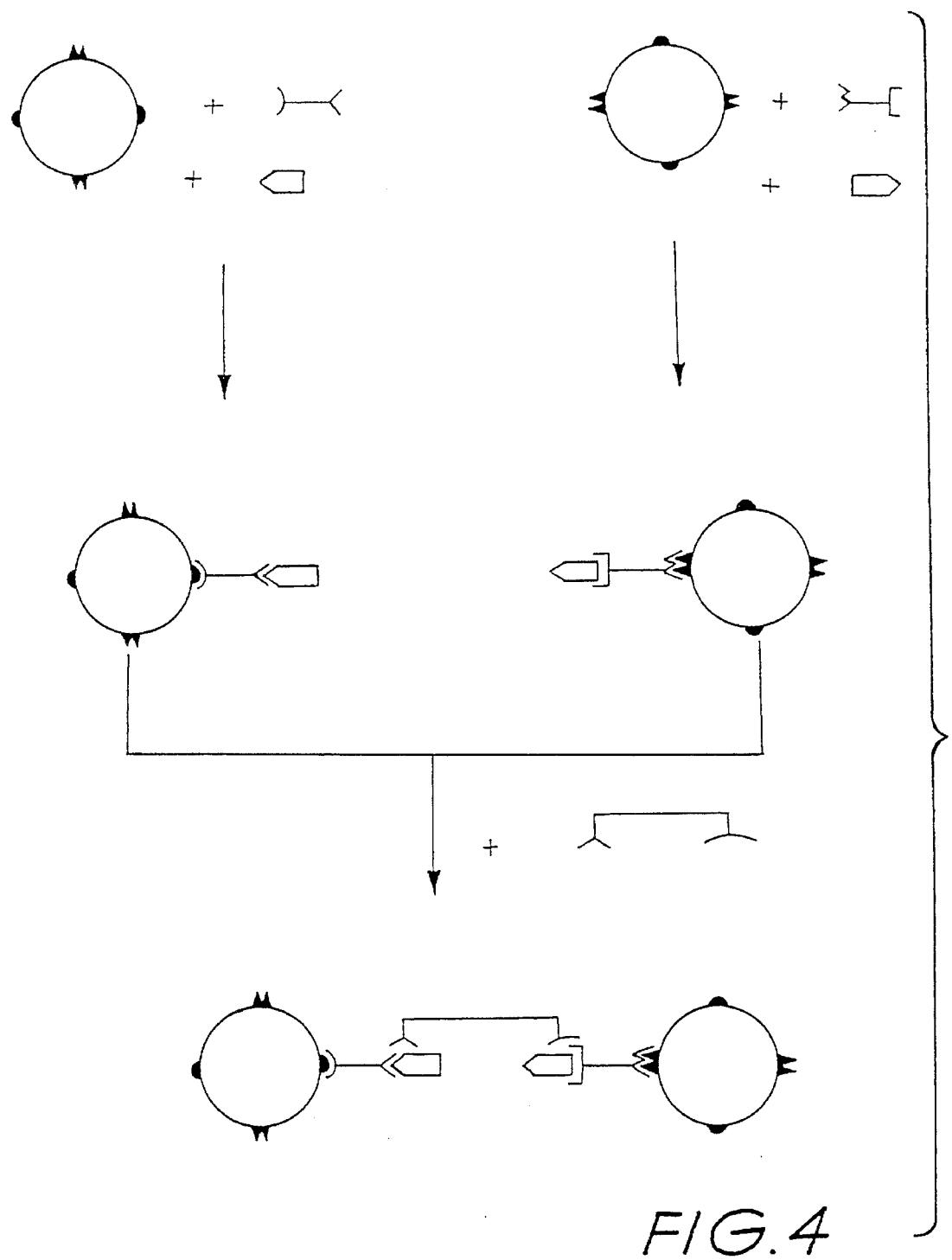
FIG. 4 illustrates uses of a secondary agglutination reagent. While drawn so as to suggest that the epitope recognized by the reagent is one generated by formation of the analyte-primary reagent complex, this is not in fact required, as may be seen in, e.g., the next Figure.
Figure 5A:
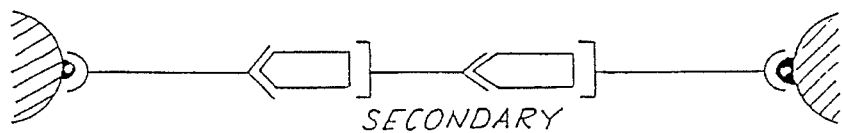
FIGS. 5(a–f) depict various ways in which the secondary agglutination reagent can bridge two analytes, including FIG. 5(a) binding the same epitopes recognized by the primary reagents, FIG. 5(b) binding a third epitope on each analyte, FIG. 5(c) binding a third and fourth epitope, on each analyte, FIG. 5(d) bridging a third epitope and an complex-formed epitope, FIG. 5(e) binding two complex-formed epitopes, and FIG. 5(f) binding an epitope recognized by a primary reagent and an epitope formed by the complexing of the analyte with the primary reagent.
Figure 5B:
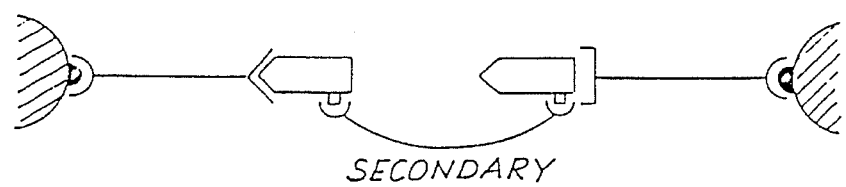
Figure 5C:
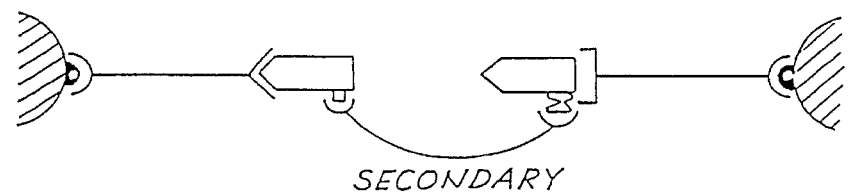
Figure 5D:
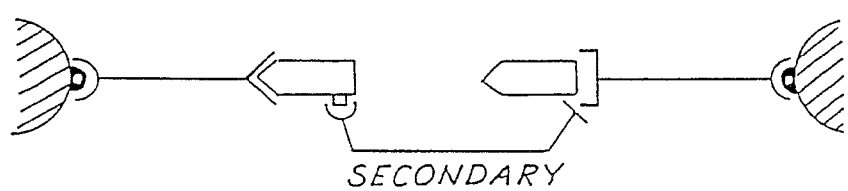
Figure 5E:
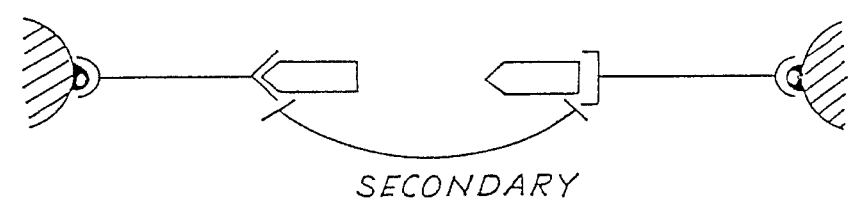
Figure 5F:
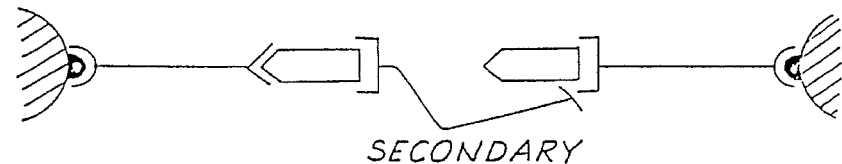
Figure 6:
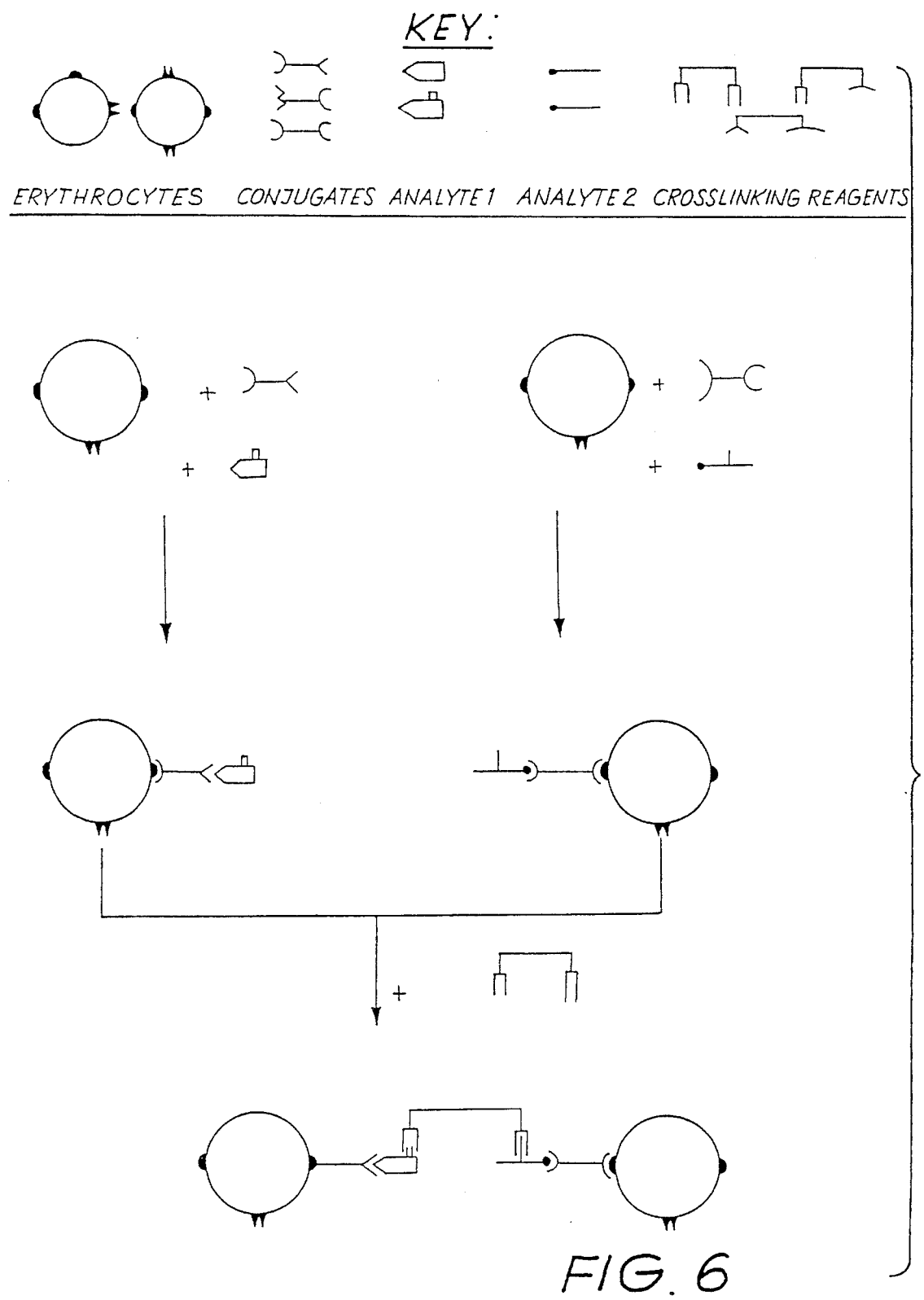
FIG. 6 shows an adaptation of the assay for simultaneous measurement of two different analytes.
Figure 7:
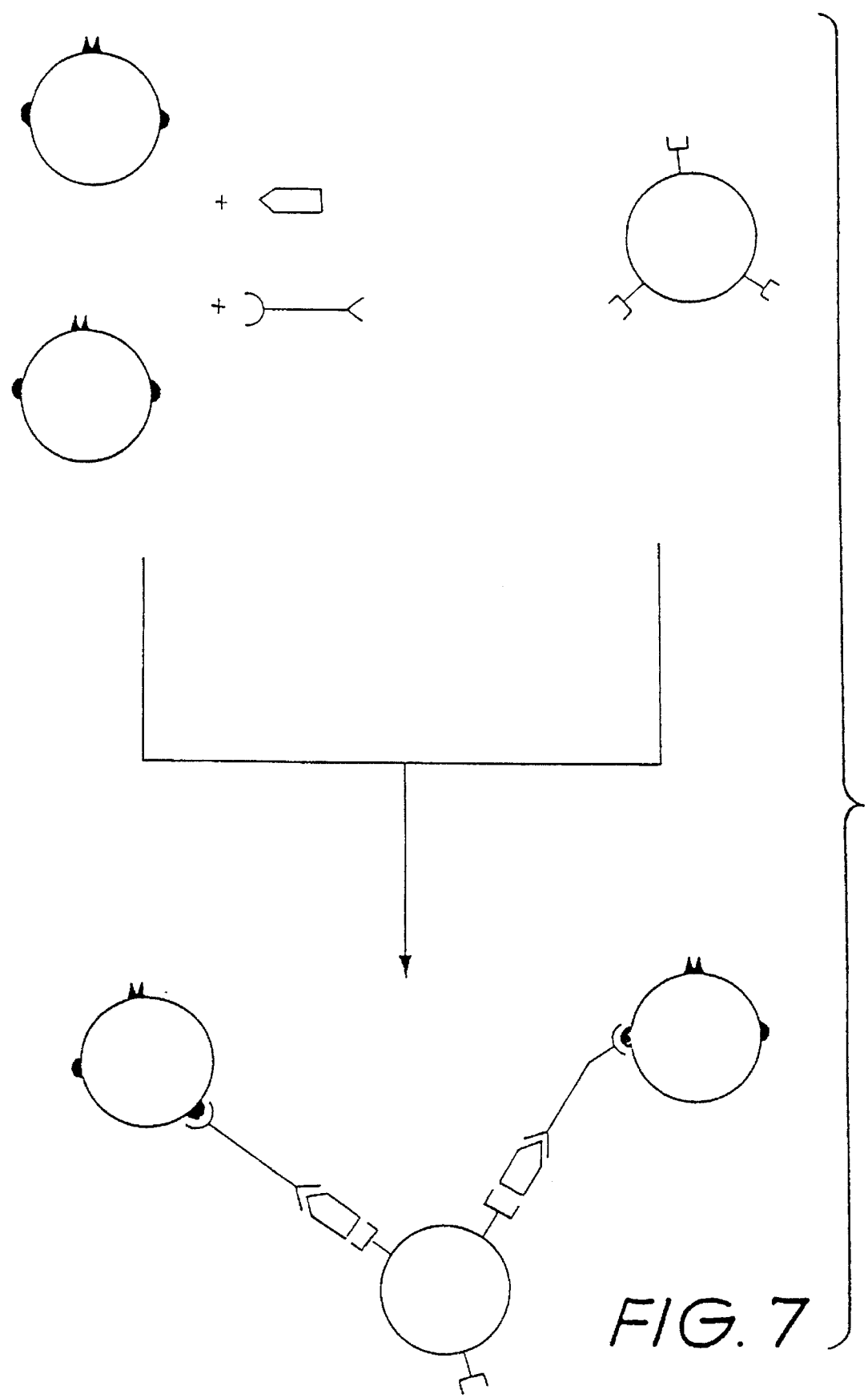
FIG. 7 illustrates use of a first primary agglutination reagent as previously described, in conjunction with a particle-bound analyte binding molecule, the latter replacing the second primary agglutination reagent.
Figure 8:
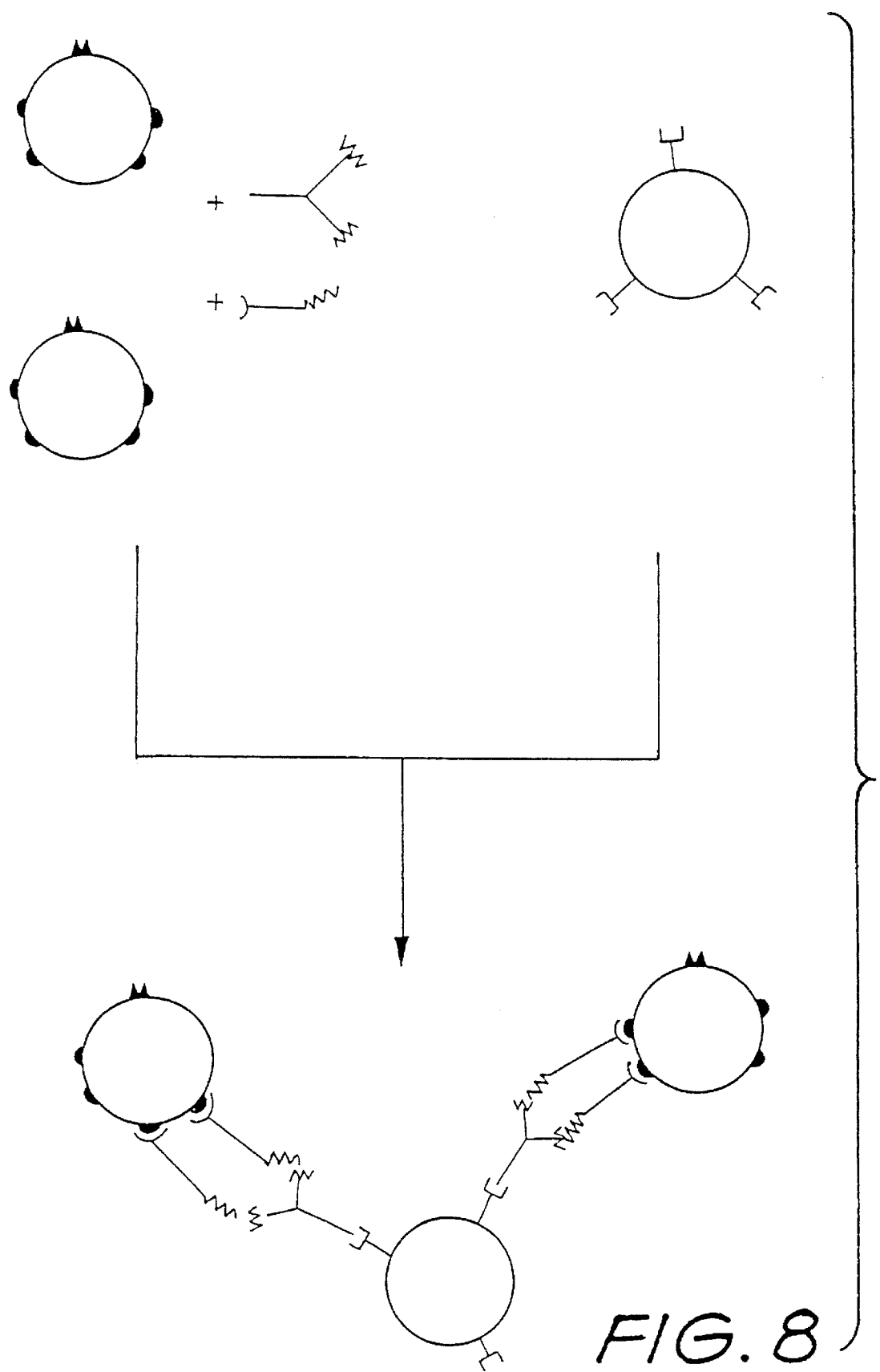
FIG. 8 depicts an assay for antibody employing a first PBM-ABM reagent wherein the analyte binding molecule is an antigen specifically bound by the analyte antibody and a second reagent which is a carrier particle bound anti-immunoglobulin. Note that this anti immunoglobulin may be covalently bound to the carrier particle (as shown) or conjugated through a particle binding moiety (such as an anti-glycophorin antibody moiety, in the case of an erythrocyte).
Figure 9:
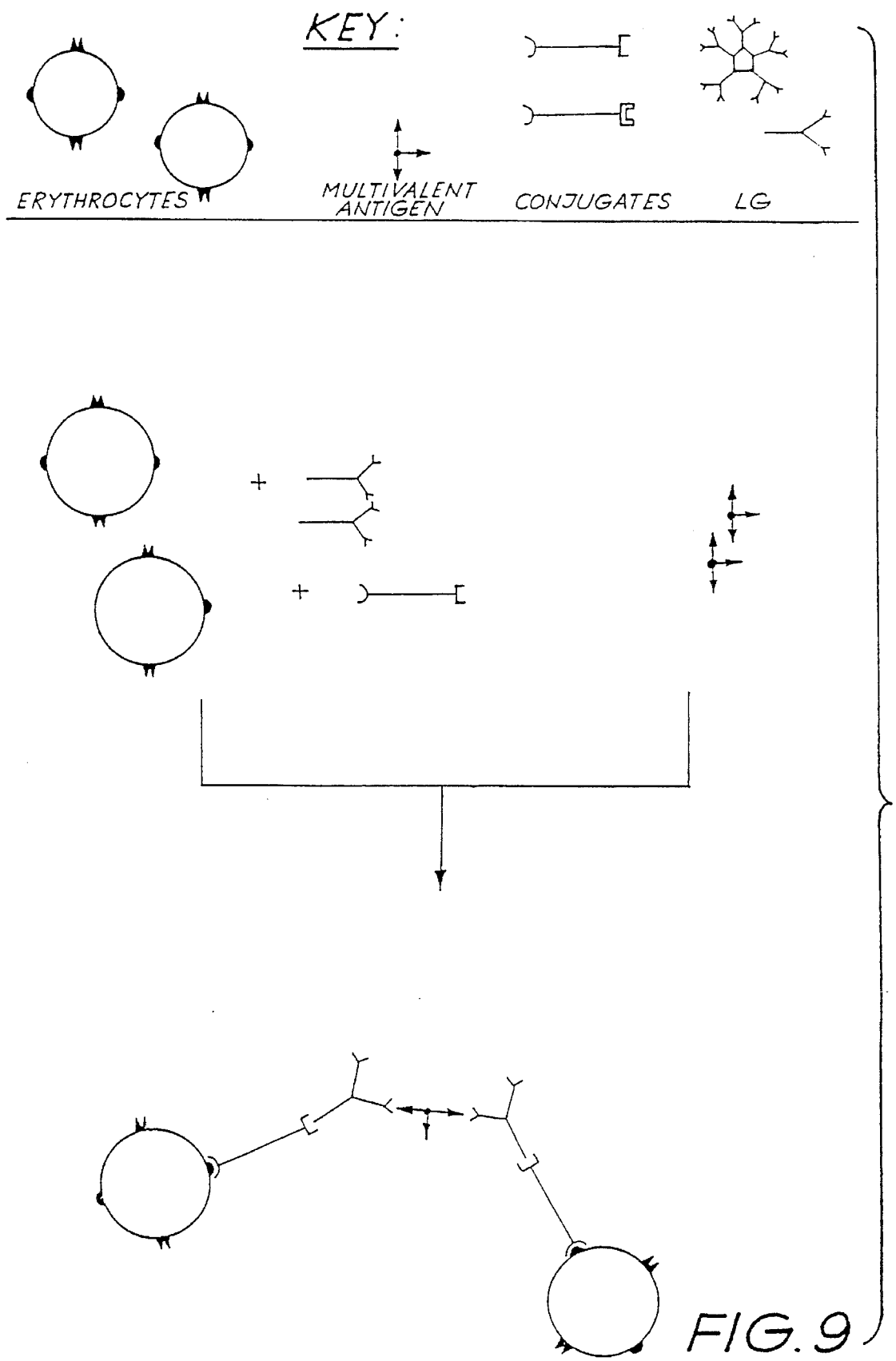
FIGS. 9 and 10 are schematic representations of a further type of assay which detects specific immunoglobulin subtypes, such as IgM or allergen-specific IgE. This assay also allows the detection of IgG antibodies to large antigens, which would be difficult to couple directly to the anti erythrocyte antibody. The EBMs can be the same or bind to different sites on the erythrocyte.
Figure 10:
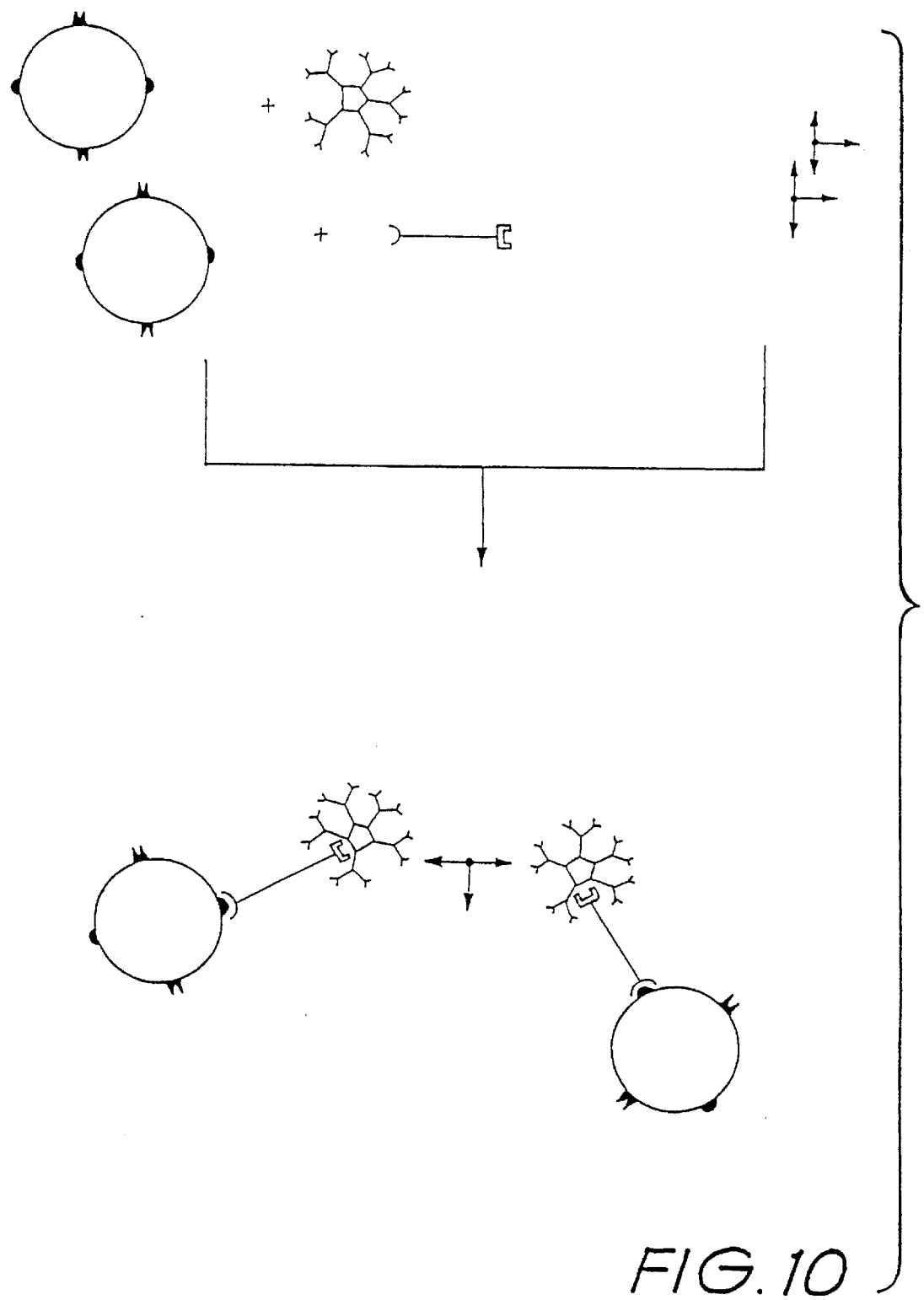

The term "epitope" is used herein to refer to a binding site on a target molecule which is specifically recognized by a binding molecule, and is not limited to binding sites recognized by antibodies.

Agglutinable Indicator Particle

Any particle which is capable of agglutination to form detectable agglutinate, and which can be provided in a form for which a specific particle binding molecule exists, may be used in the present agglutination assay. The particle may be a biological or non-biological particle, and it may be natural or artificial in origin. If natural it may be modified to render it more suitable for assay use. If artificial it may be organic or inorganic in composition. A variety of particles, including particles of latex, charcoal, kaolinite, or bentonite, as well as both microbial cells and red blood cells, have been used as agglutinable carriers (see Mochida, U.S. Pat. No. 4,308,026). A mixture of different sizes or types of particles may be used, and different particles may be used as indicators in different portions of sample. The particles may be colored or fluorescent to facilitate their visualization. The particles may be native to the sample or added to it. If added, they may be added before, during or after the aliquoting of the sample and before, during or after the addition of the agglutination reagent.

The use of erythrocytes as indicator particles was strongly criticized by Patel (U.S. Pat. No. 3,882,225) on the ground that it is difficult to standardize the indicator erythrocytes. Nonetheless, erythrocytes are preferred indicator particles. When the sample is a blood sample, it is especially preferred that the indicator particles be the erythrocytes endogenous to the sample.

There are several advantages of endogenous over exogenous erythrocytes. First, no pretreatment of endogenous erythrocytes is required. This is in contrast to methods taught in U.S. Pat. No. 4,433,059, which uses blood group 0, Rh cells, which have been centrifuged, reacted with an antibody conjugate for 15–30 minutes and washed 3 times in by centrifugation; or U.S. Pat. No. 4,668,647, which uses sheep erythrocytes which had been washed and resuspended in PBS, reacted with an antibody on a solid support, and then fixed.) Secondly, there is no need to centrifuge sample; whole blood, collected in the presence of a suitable anticoagulant, is used instead of serum or plasma. The assay is therefore more suitable for field use. For other advantages of using endogenous erythrocytes as indicator particles, see Hillyard, U.S. Pat. No. 4,894,347.

Particle Binding Moiety or Molecule (PBM)

Since, in a preferred embodiment, the particle is an erythrocyte, the preferred particle binding moiety or molecule is one which binds erythrocytes. Erythrocyte membranes are lipid bilayers with a variety of proteins. Some proteins occur only on outer portion of the membrane. Other proteins contain a hydrophobic portion allowing the protein to anchor in or pass through the membrane. A membrane-traversing protein, also called a transmembrane protein, may also have an intracellular or cytoplasmic portion. Glycophorin A is an example of a transmembrane protein.

Known proteins of erythrocyte membranes (with their blood groups shown in parentheses) include Glycophorin A (MN, Ena, Wrb), Glycophorin B (Ss, 'N', U), and the minor constituents such as integral membrane protein 1 (Rh), membrane attached glycoprotein C4 (Chido & Rodgers), integral membrane glycoprotein (anion channel), ankyrin, spectrin, protein 4.1 and F-actin. Associated with the membrane proteins are glycolipids (Lewis) and glycosphingolipids (ABH, Ii, P, Tk).

The following general publications disclosing basic information about cell membranes, in particular erythrocyte membranes, are hereby incorporated by reference: S. B. Shohet et al., The Red Cell Membrane, In: Hematology, 3rd ed. Eds: Williams et al., 1983; Marchesi, V. T. The Red Cell Membrane Skeleton, *Blood* 61:1–11, 1983.

Where the particle is an erythrocyte, there are numerous erythrocyte binding molecules (EBM), available, including antibodies, lectins, and other binding proteins. Erythrocyte membranes contain various antigenic surface constituents including proteins, glycoproteins, glycolipids and lipoproteins. Antibodies which recognize these constituents may be prepared by conventional techniques using the membrane, or the purified constituents thereof, as immunogens. These antibodies may be monoclonal or polyclonal in nature. Either the intact antibody, or specific antigen-binding fragments thereof, may be used as an erythrocyte binding molecule (EBM). The antibody or antibody fragment may be polyvalent, divalent or univalent.

A preferred EBM is an antibody (or specific binding fragment thereof) recognizing glycophorin. This molecule comprises 131 amino acids with 16 oligosaccharide chains. When erythrocyte sialoglycopeptides are extracted from membranes, the main fraction (approximately 75% of total) is glycophorin. Thus, this is an abundant moiety, which could allow antibody attachment without agglutinating the red cells. It is also readily available in a relatively pure form commercially. (for example, from Sigma Chemical Company). (See: H. Furthmayr et al., Biophys. Biochem. Res. Comm. 65:113–122 (1975)).

The design and use of conjugates of an erythrocyte binding antibody and an analyte-binding antibody as an agglutination reagent has been constrained by the need to avoid "auto-agglutination." By this term, is meant the phenomenon attributable to the ability of such a reagent, acting alone, to bind two or more erythrocytes simultaneously, and thereby to cross-link the erythrocytes into an agglutinate.

The general understanding in the art is that "auto agglutination" can be avoided only by the use of univalent erythrocyte-binding molecules. See, e.g. Chang, U.S. Pat. No. 4,533,059. Surprisingly, certain intact (e.g. bivalent or pentavalent) antibodies, notably certain anti-glycophorin mAbs, do not cause significant "auto-agglutination." It is believed that the anti-glycophorin antibody is non-autoagglutinating for steric reasons; either the antigen binding sites of the intact antibody are able only to bind adjacent epitopes on the same erythrocyte (and not span the distance between two erythrocytes) or only one of the two antigen binding sites can bind to glycophorin at one time.

When the EBM is multivalent, as is the case of a typical antibody, it is desirable that the molecule recognize an erythrocyte membrane constituent which is abundant and well distributed; the binding site should be in such a position that crosslinking between cells is inhibited by steric hindrance, thereby avoiding premature red cell agglutination. Alternatively, crosslinking may be inhibited by the selection of an EBM that recognizes a surface constituent present in sufficient quantity so that the epitopes are sufficiently close for the binding sites on the EBM to be bound by only the one erythrocyte.

One aspect of the present invention is thus the use of an intact non-auto-agglutinating anti-erythrocyte antibody (or multivalent binding fragments thereof) in conjugates in erythrocyte agglutination immunoassay. The use of such antibodies is advantageous because the conjugates are easier to prepare in high yields and there is no requirement to make Fab/Fab' fragments, which are difficult to purify to the necessary degree purity from a mixture which also contains agglutinating antibodies.

The use of univalent derivatives of these inherently non-auto-agglutinating erythrocyte-binding antibodies is also within the scope of this invention. The advantage of using non-auto-agglutinating antibody to prepare univalent binding fragments is that it is difficult to purify Fab' from a mixture of F(ab)2 and Fab' without some contamination with F(ab)2 fragments. Furthermore, some F(ab)2 "dimers" reform from the Fab univalent fragments.

If the original antibody was itself auto agglutinating, then any contaminating F(ab)2 will cause some agglutination. This will reduce the sensitivity of the assay. The problem is avoided, however, by deriving the Fab' fragments only from a non-auto-agglutinating antibody, as taught herein.

In addition, glycoproteins, glycolipids and other carbohydrate structures on the surface of erythrocytes are recognized by proteins known as lectins, which have an affinity for particular saccharides. Lectins may therefore also be used as EBMs, as contemplated by the present invention. Other molecules with specificity and affinity for the erythrocyte surface also may be used. These could also include molecules with an affinity for the lipid bilayer of the membrane. Examples of such molecules are: protamine, the membrane binding portion of the bee venom, mellitin, and other highly basic peptides.

Applicants have also discovered a new class of agglutination reagent in which the erythrocyte-binding moiety is a non-immunoglobulin peptide derived from the bee venom toxin, mellitin. Thus, the invention provides a conjugate between mellitin 7-26, or another peptide with similar nonlytic, univalent erythrocyte-binding property with an analyte-binding molecule to form a direct agglutination assay reagent. In contrast to an anti-erythrocyte antibody, mellitin 7-26 can be synthesized much more easily and economically by chemical or recombinant DNA techniques. However, the present invention is not limited to any particular method of preparing the EBM.

The preferred EBMs of the present invention will recognize erythrocyte membrane constituents found on all, or nearly all erythrocytes in a sample, so that erythrocytes endogenous to the blood sample may be used as the agglutinating particles. Such constituents include the so-called "public antigens".

The known blood group specificities are typically conferred by carbohydrate or glycolipid moieties, which are associated with membrane proteins. For its utility in the present invention, it is thus desirable that an EBM recognize either the protein part of a membrane glycoprotein constituent, which is common to all erythrocytes of a particular species, or another common structure. The ability of a divalent EBM to agglutinate erythrocytes will depend on steric factors such as the mobility of the molecule and the position of the binding sites relative to the lipid bilayer.

It is preferable but not necessary that a single EBM be used that recognizes essentially all erythrocytes. Several EBMs may be used, either in the same or in separate reagents, each of which recognizes a particular group of erythrocytes, but which in aggregate recognize essentially all erythrocytes. While it is preferable that the EBM recognize a natural surface constituent of the erythrocyte, it is possible to coat erythrocytes with a ligand recognized by the EBM, or to treat the erythrocytes so as to expose a normally cryptic ligand. Non-erythrocyte particles may likewise be functionalized so that they may be bound by an antibody or other binding molecule.

Samples and Analytes

The sample may be a biological fluid or a non biological fluid. Non-limiting examples of biological fluids obtained in vivo include whole blood, a separated blood fraction, urine, semen, saliva, cerebrospinal fluid, amniotic fluid, ascites fluid, pleural effusion, cyst fluid, pus, tissue extracts, etc. Non-limiting examples of biological fluids obtained in vitro include tissue culture supernatant, such as that of hybridoma cells, or microbial fermentation medium.

The sample may also be a non-biological fluid such as drinking water, wastewater, groundwater, or a nonaqueous fluid. Preferably, the sample is a particulate-containing sample such that the particles are suitable for use as agglutinable indicator particles. However, if the sample does not natively contain suitable particles, they may be added to the sample to obtain a "particle-containing sample". This addition may occur before, after or simultaneously with the addition of the primary agglutination reagent as described herein.

This invention is not limited to the detection of any particular analyte, however, it is especially useful for detection of analytes lacking repeating epitopes. The analyte may be a substance normally found in blood, such as a blood protein or a hormone, or it may be a foreign substance, such as a drug (including both therapeutic drugs and drugs of abuse). Typical analytes include hormones (e.g. HCG, LH, FSI1, insulin), enzymes (e.g. amylase, trypsin, CK isoforms), other polypeptides such as myoglobin, steroids (e.y. sex hormones, corticosteroids, anabolic steroids), drugs (e.g. theophylline, digoxin, paracetamol, barbiturates, cannabinoids, opioids), venoms, antibodies (e.g. of the classes IgG, IgE, IgM, etc.).

Analyte Binding Moiety or Molecule (ABM)

The analyte-binding moiety or molecule (ABM) may be any substance having a preferential affinity for the analyte, including monoclonal or polyclonal antibodies lectins, enzymes, or other binding proteins or substances (or binding fragments thereof). Where the analyte is an antigen, the ABM is usually an antibody, or an antigen-binding fragment of an antibody, such as a F(ab')2, Fab, Fv or VH fragment. Where the analyte is an antibody, the ABM is usually an antigen or hapten recognized by that antibody, or a second antibody raised against the immunoglobulin isotype of the analyte antibody.

First and Second Primary Agglutination Reagents (PBM-ABM)

The assay employs conjugates of a particle binding moiety or molecule (PBM), especially an erythrocyte binding molecule (EBM), with an analyte binding moiety or molecule (ABM). The conjugate may be a single molecule with particle and analyte-binding moieties, or a complex of two or more molecules. Hereafter, the term "molecule" will be used to cover both moieties and molecules, and "conjugate" to cover both a single hybrid molecule with two binding moieties and two conjugated molecules which each have specific binding behavior. In one embodiment, the conjugate is obtained by coupling an EBM (or other PBM) to an ABM.

The PBM and the ABM may be coupled together directly or indirectly, and by covalent or non-covalent means (or a combination thereof). Below are listed reagents and references disclosing some of the covalent coupling methods known in the art.

1. SPDP (N-Succinimidyl-3,2-(pyridyldithio) propionate) Neurath et al., 1981, J. Virol. Meth. 3:155–165.
2. MBS (m-maleimidobenzoyl-N-hydroxysuccinimide ester) Kitagawa et al., 1976, J. Biochem. 79:223 236.
3. SIAB (N-succinimidyl-4-iodoacetylaminobenzoate) Weltman et al., 1983, Bio. Techniques 1:148–152.

Selective Bifunctional Reagents

P-isothiocyanatobenzoylchloride
(U.S. Pat. No. 4,680,338)
Bifunctional Reagents

1. BSOCOES—Bis[2 -(succinimidooxycarbonyloxy-)ethyl]sulfone Zarling et al., 1980, J. Immunol. 124:913–920.
2. BS—Bis(sulfosuccinimidyl)suberate Staros, 1982, Biochemistry 21:3950–3955.

Other Reagents

1. Glutaraldehyde—Avrameas, 1969, Immunochem. 6:43.
2. Periodate Oxidation—Nakane et al., 1974, J. Histochem. Cytochem. 22:1084–1091
3. Carbodiimide
4. Disulfide Exchange The PBM and the ABM may also be coupled noncovalently, for example, by (a) attaching biotin to one and avidin (or streptavidin) to the other), (b) attaching an anti antibody to one, which then binds the other, (c) attaching Protein A to one, which then binds the Fc portion of the other, or (d) attaching a sugar to one and a corresponding lectin to the other.

It should be understood that, in coupling the PBM and the ABM, the binding characteristics should be changed as little as possible. It may be advantageous to provide a spacer moiety between the PBM and the ABM to reduce steric hindrance.

The PBM/ABM conjugate may be a hybrid antibody. One method of constructing such a conjugate is the following:
 (a) preparing F(ab)'2 fragments of a selected antibody by pepsin digestion;
 (b) reducing and treating the fragments with Ellman's reagent to produce Fab' fragments of the selected antibody;
 (c) thiolysing a selected analyte-specific antibody or a selected anti-erythrocyte antibody; and
 (d) coupling the thioylated Fab' fragment to the Ellman's reagent-treated Fab' fragment to produce a hybrid anti-erythrocyte antibody antigen specific antibody conjugate.

Another method for constructing an EBM/ABM conjugate, in the form of a chimeric antibody, comprises:
 (a) treating an anti-erythrocyte mAb-producing hybridoma and an analyte-specific mAb-producing hybridoma with a distinct site-specific irreversible inhibitor of macromolecular biosynthesis; preferably the inhibitor is selected from the group consisting of emetine, actinomycin D, hydroxyurea, ouabain, cycloheximide, edine and sparsomycin;
 (b) fusing the two different mAb-producing hybridomas with polyethylene glycol to produce a heterohybridoma;
 (c) cloning the fused cells by any of a number of cloning methods such as isolation in soft agarose or by limiting dilution;
 (d) selecting cloned heterohybridomas secreting chimeric anti-erythrocyte antibody-antigen specific antibody with a screening assay appropriate to the antibodies;
 (e) purifying the antibody product by affinity purification to free it from non-chimeric antibodies. The hybrid or chimeric antibody of the present invention thus comprises two "half molecules," one with specificity for erythrocytes (the EBM) and the other with specificity for the analyte (the ABM). In this case the antibody's own disulfide bonds couple the ABM to the EBM to form an appropriate conjugate.

Such a hybrid antibody has advantages over a tail-to-tail conjugate as taught in the prior art, which is formed by a bifunctional coupling agent, conjugating an anti-analyte antibody and a univalent fragment of anti-erythrocyte antibody. The advantages include ease of preparation, the preservation of the correct stoichiometry and stereochemistry of both antibodies and the retention of the binding affinity of each fragment.

When the analyte-binding molecule is also a peptide or protein, the use of a peptide to bind the erythrocyte has the further advantage that the entire conjugate may be prepared without any need for a bifunctional coupling agent. Instead, a DNA sequence encoding the erythrocyte-binding peptide and the analyte-binding peptide as a single transcriptional unit is provided, and the desired conjugate is expressed as a fusion protein, with the two moieties joined by a simple peptide bond, or with a peptide spacer of desired length. One particularly preferred example is a DNA sequence encoding an erythrocyte-binding antibody fragment (which could be just the binding site, not a complete Fab) and analyte antibody (which could be just the binding site, not a complete Fab) or antigen as a single transcriptional unit is provided, and the desired conjugate is expressed as a fusion protein, with the two moieties joined by a simple peptide bond, or with a peptide spacer of desired length. Alternatively, the divalent peptide may be prepared by direct chemical synthesis.

As intended herein, the particles in or added to the samples assayed according to the methods of the present invention have a plurality of binding sites.

The first and second primary agglutination reagents may recognize the same or different binding sites (epitopes) on the surface of the particle, and may be prepared by the same or different procedures.

Secondary Agglutination Reagent (CBM-CBM)

The secondary agglutination reagent, as previously stated conjugates the first complex (formed by the particles and analyte of the first sample portion and the first primary agglutination reagent) and the second complex. It thus possesses two complex-binding moieties or molecules (CBM).

The CBMs may be the same or different, and they may bind to an epitope found on the analyte originally, or one generated by the binding of an ABM-PBM conjugate to its analyte epitope. This epitope may be the same epitope as is recognized by the PBM-ABM conjugate, or a different analyte epitope. The same techniques may be used to prepare the secondary agglutination reagent as were described for the primary reagent.

Test Kits

Test kits for use in the present invention comprise first and second EBM-ABM conjugates as previously described, and may optionally include a third reagent as described.

Assay Formats

In a preferred embodiment, the contemplated direct agglutination assay comprises:

(a) dividing the sample into a first portion and a second portion;

(b) forming a first mixture of a first primary agglutination reagent comprising a particle binding molecule (PBM) and an analyte binding molecule (ABM1) capable of binding to a first binding site of the analyte, a first sample portion and agglutinable particles;

(c) forming a second mixture of a second primary agglutination reagent comprising a particle binding molecule or moiety and an analyte binding molecule or moiety (ABM2) capable of binding to a second and different binding site of the analyte, a second sample portion, and agglutinable particles; and (d) mixing the first mixture with the second mixture to obtain a third mixture, wherein agglutination of the third mixture indicates the presence of the analyte in the sample.

Surprisingly, the separate mixing according to the above embodiment has been found to increase the sensitivity by as much as 20- to 30-fold as compared to an assay where two conjugates are mixed together with a single blood sample such as in the assay described by the present inventors in Australian Patent Application No. 24182/88 and U.S. Pat. No. 4,894,347.

It should be understood that this embodiment relies on the fact that the PBM is present in excess compared with the number of antigenic molecules being detected. The PBM should thus recognize an particle surface epitope which is abundant.

The affinity of the interactions does not appear to be a significant factor at analyte concentrations likely to be present in a blood sample. The basis for the increased sensitivity using the two spot system is more likely to be stoichiometric. Thus, in the assay of Example, there were 10 ug/mL of anti-erythrocyte antibody conjugate and approximately 700,000 glycophorin molecules on the surface of a red cell and the amounts of HCG being measured was in the order of 25–100,000 IU/L or 2.5–1.0000 mg/L. The molecular weight of HCG is about 50 kDa and that of the conjugate is about 100 kDa. Therefore, many more conjugate molecules are bound to erythrocyte surfaces than there are HCG molecules in the blood sample. Affinity may have some influence; analysis of a series of antibody conjugates with varying affinities for HCG indicated a decrease in sensitivity with decreasing affinity.

The anti-erythrocyte antibody has an affinity of $1 \times 10^9$ and the highest affinity for HCG was $5.9 \times 10^9$.

When we speak of forming a mixture of several components, the component may be brought together simultaneously, or sequentially in any order.

When one of the components of a formed mixture is a set of agglutinable particles and another component is a portion of a sample, it should be understood that the particles may be endogenous to the sample so that, in effect, sample analyte and agglutinable particles are mixed simultaneously with the remaining reaction component(s), or the particles may be exogenous, in which case they may be added before or after the division of the sample, and at any stage in the formation of the recited mixture.

For the measurement of monoepitopic haptens, such as drugs or steroids, one may use two conjugates, one consisting of anti-erythrocyte antibody/antihapten antibody and the other anti-erythrocyte antibody/antibody to the hapten:antihapten immune complex.

This assay thus comprises:

(a) dividing the sample into a first and a second portion;

(b) forming a first mixture of a first primary agglutination reagent comprising a particle binding molecule and an analyte-binding molecule capable of binding to the binding site, and thereby forming a second binding site, a first sample portion and agglutinable particles;

(c) forming a second mixture of a second primary agglutination reagent comprising a particle binding molecule and an analyte-binding molecule capable of binding to the second binding site a second sample portion and agglutinable particles; and then (d) mixing the first mixture with the second mixture to obtain a third mixture, wherein agglutination of the third mixture indicates the presence of the analyte in the sample.

The second epitope may comprise at least part of the first epitope bound by the first analyte-binding molecule or may result from a conformational change taking place in the analyte molecule upon binding the first analyte-binding molecule.

In a further enhancement of these two basic embodiments, the first and second mixtures may be mixed with secondary agglutination reagent. Use of a secondary reagent makes it less important to employ an agglutinable particle with a large number of non-overlapping epitopes. Six different (and non-limiting) types of secondary reagents which can be used in this version of the assay are described below.

(1) A dimeric analyte-binding molecule capable of binding to a third site on each analyte molecule.

(2) A divalent hybrid analyte-binding molecule capable of binding to a third site on one analyte molecule and a fourth site on the other analyte molecule.

(3) A divalent hybrid analyte-binding molecule capable of binding to a third site on one analyte molecule and to a fourth site which is generated by the binding of an analyte-binding molecule to a binding site on another analyte molecule.

(4) A divalent hybrid analyte-binding molecule capable of binding to a site generated by the binding the first analyte-binding molecule (of a primary reagent) to a first analyte molecule, and to a site generated by the binding of the second analyte binding molecule to a second molecule of analyte.

(5) A divalent hybrid analyte-binding molecule capable of binding to the first binding site of the analyte and to the second binding site of the analyte.

(6) A divalent hybrid analyte binding molecule capable of binding to the second binding site of the analyte and to a site generated by the binding of the second analyte binding molecule to the second binding site.

In another embodiment, the invention is directed to a two site direct agglutination assay for the detection of the simultaneous presence of two different analytes in a particle containing sample wherein the first and second analytes each comprise at least one analyte-binding site, the assay comprising:

(a) dividing the sample into a first portion and a second portion;

(b) forming a mixture of a first primary agglutination reagent comprising a particle binding molecule and a first analyte-binding molecule capable of binding to a first binding site on the first analyte, the first sample portion, and agglutinable particles;

(c) forming a second mixture of a second primary agglutination reagent comprising a particle binding molecule and a second analyte-binding molecule capable of binding to a second binding site on the second analyte, the second sample, and portion and agglutinable particles;

(d) mixing the first mixture with the second mixture and with a secondary agglutination reagent wherein agglutination of the combined mixtures in the presence of the secondary agglutination reagent indicates the presence of both the first and second analytes in the sample.

For this embodiment, the secondary agglutination reagent must be heterobispecific. Generally, mixing of the first conjugate with the first sample and the second conjugate with the second sample are performed over a 1–2 minute interval. The first mixed sample and the second mixed sample are typically mixed together for 1–2 minutes. A strong positive test will show agglutination in 10–20 seconds.

In a variation of the various embodiments of the contemplated direct agglutination assay, the blood is mixed with the first ABM-EBM conjugate. A second reagent is added, which comprises an added particle, such as exogenous red blood cells bound to a conjugate of an EBM and a different ABM which binds to a different site on the analyte. The latter reagent can also be an added particle, such as latex or exogenous red blood cells to which an ABM, which binds to a different site on the analyte, has been coupled chemically. It will be appreciated that the function of particle/ABM and particle:EBM ABM is the same, vis-a-vis the binding of analyte.

In the agglutination assay for an antibody analyte described by Hillyard, a whole blood sample containing the analyte (and endogenous erythrocytes serving as the indicator particle) is reacted with an EBM-ABM conjugate, wherein the ABM is typically an antigen specifically bound by the antibody or a second, anti-idiotypic antibody against the analyte antibody. We have found that the sensitivity of such an assay may be increased by adding a second, particle-bound, (analyte antibody)-binding reagent. The analyte-binding moiety of this latter reagent is typically an anti-Fc antibody. It may be bound to the particle either covalently through its own Fc, or by a particle-binding moiety conjugated covalently or noncovalently to the analyte binding moiety. If all of the analyte in the sample is bound by the first reagent, the second reagent, by binding to the analyte will form additional interparticle connections.

The sensitivity of assays for analytes with repeating epitopes is likewise reduced by the formation of multiple bridges between the indicator particle and the analyte, though with such assays only a single PBM-ABM reagent is necessary for agglutination. The method of this invention may be applied to such analytes by deliberately ignoring any repeating epitopes of the analyte, and instead identifying and providing binding molecules for two different nonrepeating epitopes thereof.

Moreover, the present method may provide some advantage in assaying an analyte for which there is an epitope which, while repeating, is uncommon, though the increase in sensitivity will be less pronounced.

In another embodiment of this invention there is provided an assay which detects antibodies of a particular immunoglobulin isotype, such as, for example, IgM, or allergen specific IgE antibodies. This assay also allows the detection of IgG antibodies to large antigens which would be difficult or impossible to couple directly to an anti-erythrocyte antibody. The EBMs can be the same or bind to different sites on the erythrocyte.

One reagent comprises bispecific anti-erythrocyte (or other particle)—anti IgE antibody, which binds to only one site on the IgE molecule. The other is the allergen, a multivalent moiety, added either alone or bound to a carrier substance such as a latex particle or a protein. Agglutination occurs when IgE antibodies specific to the allergen are present in the sample.

Similarly, for detection of a specific IgM antibody, the reagents are a bispecific anti-erythrocyte—anti IgM conjugate, (which binds to only one site on the IgM molecule) and a multivalent antigenic reagent added either alone or bound to a carrier substance such as a latex particle or a protein. Agglutination occurs when IgM antibodies specific to the antigen are present in the sample.

Having now generally described the invention, the same will be more readily understood through reference to the following examples which is provided by way of illustration, and are not intended to be limiting of the present invention, unless specified.

EXAMPLE 1

Preparation of an Erythrocyte Binding Molecule (EBM): Anti-Glycophorin Antibody

Mice were immunized with human erythrocytes and mAbs produced by fusing the spleen cells of immunized animals with mouse myeloma cells, according to methods well-known in the art. Hybridoma supernatants were screened for the presence of the desired antibody by both spin agglutination assay and enzyme immunoassay (EIA), wherein glycophorin was bound to polystyrene in a microtiter plate.

Spin agglutination was performed by a modification of Wyatt et al. (Aust. J. Med. Lab. sci. 4:48–50 (19)). 50 ul of cell culture supernatant was mixed with 50 ul of a 1% erythrocyte suspension in a microtiter plate. Antibodies which bound glycophorin, but did not agglutinate, were selected.

For EIA, microtiter plates were coated with 10 ug/ml human glycophorin (Sigma Chemical Co., Cat. No. G-73B91), washed and then incubated with serial dilutions of the mAb. After further washing, the presence of bound antibody was determined by the addition of an enzyme-labelled second antibody (specific for murine immunoglobulin), followed by the addition of substrate for the enzyme. The antibody titer was determined to be the greatest dilution of hybridoma supernatant which gave an absorption (A420) reading greater than 0.17 units above background.

Of 384 wells, 40 primary clones were chosen. Each clone fell into one of three categories: a positive result in the spin agglutination assay only, binding to glycophorin in EIA only, or both reactions, as depicted in Table 1.

TABLE 1

| EIA | Spin agglutination | Number of clones |
| --- | --- | --- |
| Negative | Positive | 4 |
| Positive | Positive | 20 |
| Positive | Negative | 16 |

Subsequent absorption studies were performed to confirm that the mAbs recognized a glycophorin domain exposed on the erythrocyte surface.

The hybridoma cells producing mAbs having the desired reactivities were grown in vivo by intraperitoneal injection into mice according to methods well known in the art. The ascites fluids, containing the secreted mAbs, were clarified by centrifugation and screened.

The results of the screening assays of ascites fluids containing various mAbs are shown in Table 2, below:

TABLE 2

Glycophorin Reactivity of Monoclonal Antibodies

| Clone | Ascites Fluid Titer Spin Agglutination | Glycophorin EIA | Red Cell Absorption |
| --- | --- | --- | --- |
| RAT 1D3/167 | 512000 | <1000 | Positive |
| RAT 3D6/5 | 6400 | 1024000 | Positive |
| RAT 1C3/86 | <1000 | 1024000 | Positive |
| RAT 3B1/172 | 256000 | 2000 | Positive |
| RAT 3D3/22 | 4000 | 1024000 | Positive |
| RAT 3D5/61 | 128000 | 1024000 | Positive |
| RAT 1A2/187 | <1000 | 256000 | Positive |
| RAT 2A2/187 | <1000 | 128000 | Positive |
| RAT 1A3/129 | <1000 | 12800 | Weak |
| RAT 1C4/5 | <1000 | 128000 | Positive |
| RAT 4C3/13 | <1000 | 128000 | Positive |
| RAT 3B1/70 | <1000 | 517000 | Positive |

RAT 1C3/86 was selected and deposited under the Budapest Treaty at the American Type Culture Collection (12301 Parklawn Drive, Rockville, Md., 20852) on 7 Sep. 1988. The cell line has the designation G 26.4.IC3/86, and received the ATCC accession number HB9893.

MAbs were purified to homogeneity from ascites fluids by chromatography on hydroxyapatite (Stanker et al., J. Immunol. Meth. 76:157 (1985)).

EXAMPLE 2

Preparation of Chimeric Antibodies (Anti-Glycophorin/Anti-Human Chorionic Gonadotropin, hCG) and Use in Assay for hCG Monoclonal antibodies reacting with both the beta subunit of hCG and with the complete molecule were prepared by methods well known in the art. Hybridoma supernatants were screened for the presence of desired antibody by enzyme immunoassay wherein the beta subunit of hCG, the alpha subunit and intact hCG were bound to polystyrene in a microtitre plate essentially as described in Example 1.

The results of screening assays of ascites fluids containing various MAbs are shown in Table 3.

| | ENDPOINT TITRES | | |
| --- | --- | --- | --- |
| | alpha subunit | beta subunit | whole molecule |
| HCG 2A1/67 | <1000 | 10280000 | 512000 |
| HCG 2C1/4 | <1000 | <1000 | 64000 |
| HCG 3D2/34 | <1000 | 128000 | 128000 |
| HCG 1A3/61 | <1000 | 512000 | 512000 |
| HCG 2B5/34 | <1000 | 1000 | 128000 |
| HCG 2B4/98 | <1000 | <1000 | 256000 |

MAb's were purified to homogeneity from ascitic fluids by chromatography on hydroxylapatite (Stanker et al J. Immunol. Meth 76 157 1985).

Monoclonal antibodies RAT 1C3/86 (anti-human red blood cell) and HCG-2A1/67 and HCG-1A3/63 (anti-human hCG) were digested with pepsin essentially as described by Hackman, et al., 1981, Immunology, 15, 429–436, and purified by chromatography on a TSK-3000 SW column. 2 mg RAT 1C3/86 was digested for 45 minutes with 1% w/w pepsin in a buffer containing 0.1M acetic acid, 70 mM sodium chloride pH 3.5. Meanwhile, 2 mg HCG 2A1/67 and 2 mg HCG 1A3/63 were digested with 1% w/w pepsin for 2 hours in the same buffer. The reactions were terminated by the addition of 1.5M Tris to raise the pH to 8. The F(ab)$_2$ fragments were purified by gel filtration chromatography on a TSK-3000 SW column.

Reduction of the F(ab)$_2$, and subsequent blocking of the Fab fragment, was carried out as described by Brennan, et al., 1985, Science 229, 81–83. A 3 mg/ml F(ab)$_2$ preparation was treated with 1 mM mercaptoethylamine, in the presence of 10 mM sodium arsenite, for 16 hours at 25 C. The Fab fragments were stabilized by reaction with 5,5'-dithiobis, (2-nitrobenzoic acid) (Ellman's reagent) for 3 hours at 25 C. The Fab fragment was then purified by gel filtration chromatography on a TSK-3000 SW column.

The thiol forms of HCG 2A1/67 and HCG 1A3/63 were regenerated by reaction with 10 mM mercapthelylamine for 30 minutes at 25 C. Excess reagent was removed by gel filtration chromatography on a TSK-3000 SW column. Separately the thiol form of each of the HCG antibodies and the Ellman's reagent-treated RAT-1C3/86 were incubated for 16 hours at 25 C. as described by Brennan et al. The chimeric antibodies thus formed were finally purified by gel filtration chromatography on a TSK-3000 SW column.

EXAMPLE 3

"Two Drop" Agglutination Assay for HCG

Reagent 1: 10 ug/ml of Conjugate A (a hybrid antibody consisting of "half" erythrocyte-binding antibody, RAT 1C3/86, and "half" HCG-specific antibody A) in PBS, pH 7.4, containing 1 mg/ml BSA and 0.010% sodium azide.

Reagent 2: 10 ug/ml of Conjugate B (a hybrid antibody consisting of "half" erythrocyte-binding antibody, RAT 1C3/86, and "half" HCG specific antibody B) in PBS, pH 7.4, containing 1 mg/ml BSA and 0.01% sodium azide.
Method The method requires two small drops of blood, one of which is first mixed with conjugate 1, the other with conjugate 2. (These two drops are thus the "first and second sample portions" as previously described.) After an incubation period, the two drops are then mixed together. Two 5 ul samples of whole blood were placed on a slide about 1 cm apart. 10 ul of reagent 1 was added to one and mixed with a small stirring rod (e.g., a toothpick) to form a small circle. 10 ul of reagent B was added to the second sample and mixed in a similar manner.

The sensitivity of the test will be lower should the two samples be mixed accidentally before the conjugates have bound to the erythrocytes.

The agglutination plate was then rocked gently for 30 seconds and the two pools combined by mixing with a toothpick. The mixture was then rocked gently for a further 2 minutes and the extent of agglutination determined.

This method can, of course, be automated or adapted to a single use device. Upon comparison of "two drop" and "one drop" assays at various dilutions, it was apparent that in each case the visible agglutination response of each sample assayed by the "two drop assay" of the invention was much stronger than for the corresponding sample assayed by the "one drop assay".

EXAMPLE 4

"One Drop" Particle Carrier Assay for HCG

Reagent: 10 ug/ml of conjugate A (as in Example 3), a 0.5% suspension of latex particles (polystyrene, 0.8 um diameter) coated with HCG-specific antibody B, 1 mg/ml BSA in PBS containing 0.01% azide.
Method The method only requires one drop of blood and provides similar sensitivity to the assay of Example 3. To 10 ul of blood, 25 ul of test reagent was added and mixed with a small stirring rod, rocked gently for a further 2 minutes, and the presence or absence of agglutination was noted.

EXAMPLE 5

Preparation of Melittin as an Alternative EBM

A peptide from bee venom, mellitin (amino acid sequence: CVLTTGLPALISWIKRKRQQ), was used as an alternative to the erythrocyte-binding mAb. This peptide binds to the erythrocyte surface without lysing the cell (deGrado W. F. et al., J. Amer. Chem. Soc. 103:679–81 (1981)). The peptide was synthesized by the Merrifield procedure (Hodges et al., Anal. Biochem. 65:241 (1975)).

One advantage of using mellitin as the EBM is that mellitin and a peptide-type ABM may be synthesized as a single unit, having both erythrocyte and analyte binding activity in the single peptide.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

We claim:

1. A direct agglutination assay for the detection of an analyte in a sample, wherein the analyte includes a first nonrepeating epitope and a second nonrepeating epitope, the assay comprising:

(a) providing first and second primary agglutination reagents, each of which is capable of binding simultaneously to an agglutinable particle, and to a nonrepeating epitope of said analyte, said first and second reagents binding to different, non-overlapping, nonrepeating epitopes of said analyte;

(b) forming a first mixture of a first sample portion, an excess of said first reagent relative to said analyte, and agglutinable particles bindable by said first reagent;

(c) forming a second mixture of a second sample portion, an excess of said second reagent relative to said analyte, and agglutinable particles bindable by said second reagent; and (d) forming a third mixture by mixing said first and second mixtures, wherein said first and second sample portions are substantially equal in size, wherein the rate of reaction between said first reagent and the analyte of said first sample portion, and between said second reagent and the analyte of said second sample portion are substantially equal, and wherein agglutination in the third mixture indicates the presence of the analyte in the sample.

2. The assay of claim 1 wherein said sample is whole blood.

3. The assay of claim 2 wherein said first and second reagents have agglutinable particle binding molecules which is an anti-erythrocyte antibody or a specifically binding fragment thereof.

4. The assay of claim 3 wherein said antibody is an anti-glycophorin antibody or a specifically binding fragment thereof.

5. The assay of claim 1 wherein the agglutinable particles are endogenous to the sample.

6. The assay of claim 1 wherein the agglutinable particles are exogenous to the sample.

7. The assay of claim 1 wherein said sample is selected from the group consisting of whole blood, a separated blood fraction, urine, semen, saliva, cerebrospinal fluid, amniotic fluid, ascites fluid, pleural effusion, cyst fluid, pus and tissue extracts.

8. The assay of claim 6 wherein the agglutinable particles are selected from the group consisting of latex, charcoal, kaolinite, bentonite, microbial cells and red blood cells.

9. The assay of claim 1 wherein the first primary agglutination reagent binds to a different epitope on the agglutinable particles from that of the second primary agglutination reagent.

10. A direct agglutination assay for the detection of an analyte in a sample, wherein the analyte includes a first binding site, the assay comprising:
    (a) providing a first primary agglutination reagent which is capable of binding to an agglutinable particle and to said analyte epitope, and which when bound to said analyte epitope forms a second epitope;
    (b) forming a first mixture of a first sample portion, said first reagent, and agglutinable particles bindable by said first reagent;
    (c) providing a second primary agglutination reagent which is capable of binding to an agglutinable particle and to said second epitope;
    (d) forming a second mixture of a second sample portion, said second reagent, and agglutinable particles bindable by the second reagent, said second epitope being bindable by said second reagent; and
    (e) forming a third mixture by mixing said first and second mixtures,
    wherein agglutination in the third mixture indicates the presence of the analyte in the sample.

11. The assay of claim 10 wherein said sample is whole blood.

12. The assay of claim 1 wherein said first and second reagents have agglutinable particle binding molecules which are the same.

13. The assay of claim 1 wherein said first and second reagents have agglutinable particle binding molecules which are different.

14. The assay of claim 1, further comprising reacting the third mixture with a secondary agglutination reagent, said secondary reagent being bispecific, each combining sites of said secondary reagent being specific for an epitope selected from the group consisting of an epitope of said analyte and an epitope formed by the binding of the primary reagent to said analyte.

15. The assay of claim 5, further comprising reacting the third mixture with a secondary agglutination reagent, said secondary reagent being bispecific, each combining sites of said secondary reagent being specific for an epitope selected from the group consisting of an epitope of said analyte and an epitope formed by the binding of the primary reagent to said analyte.

16. The assay of claim 10 wherein the agglutinable particles are endogenous to the sample.

17. The assay of claim 10 wherein the agglutinable particles are exogenous to the sample.

18. The assay of claim 17 wherein the agglutinable particles are selected from the group consisting of latex, charcoal, kaolinite, bentonite, microbial cells and red blood cells.

19. The assay of claim 10 wherein the first primary agglutination reagent binds to a different epitope on the agglutinable particles from that of the second primary agglutination reagent.

20. A two site direct agglutination assay for the detection of the simultaneous presence of two different analytes in a sample wherein the first and second analytes each comprise at least one analyte-binding site, the assay comprising:
    (a) providing a first primary agglutination reagent which is capable of binding simultaneously to an agglutinable particle and to said first analyte;
    (b) providing a second primary agglutination reagent which is capable of binding simultaneously to the same or a different type of epitope on an agglutinable particle and to said second analyte;
    (c) providing agglutinable particles to which said first and second primary agglutination reagents can bind, if such particles are not already present in the sample;
    (d) forming a first mixture of a first sample portion, said first agglutination reagent, and bindable agglutinable particles to obtain first analyte:first agglutination reagent:particle complex;
    (e) forming a second mixture of a second sample portion, second primary agglutination reagent, and bindable agglutinable particles to obtain second analyte:second reagent:particle complex;
    (f) providing a secondary agglutination reagent which can bind simultaneously to both said first complex and to said second complex, in each case being specific for either a native epitope of the analyte or an epitope formed by the binding of the primary reagent to said analyte, but not able to bind to two complexes of the same analyte;
    (g) forming a third mixture of said first and second mixtures and said secondary agglutination reagents wherein agglutination of said third mixture indicates the simultaneous presence of said first and second analytes in the sample.

21. A direct agglutination assay for the detection of an analyte in a sample, wherein the analyte includes a first nonrepeating epitope and a second nonrepeating epitope, the assay comprising:
    (a) providing a first primary agglutination reagent which is capable of binding simultaneously to an endogenous agglutinable particle, and to a nonrepeating epitope of said analyte;
    (b) forming a first mixture of a first sample portion, said first reagent, and agglutinable particles bindable by said first reagent;
    (c) providing a primary agglutination agent comprising a second primary exogenous agglutination reagent:agglutinable particle complex wherein said second primary agglutination reagent is capable of binding to a nonrepeating epitope of said analyte and said first and second reagents binding to different, non-overlapping epitopes of said analyte;

(d) forming a second mixture of said first mixture and said agent, and agglutinable particles bindable by said first reagent;

wherein agglutination in the second mixture indicates the presence of the analyte in the sample.

22. A direct agglutination assay for the detection of an analyte in a sample, wherein the analyte includes a first binding site, the assay comprising:

(a) providing a first primary agglutination reagent which is capable of binding to an agglutinable particle and to said analyte epitope, and which when bound to said analyte epitope forms a second epitope;

(b) forming a first mixture of a first sample portion, said first reagent, and agglutinable particles bindable by said first reagent;

(c) providing a primary agglutination agent comprising a second primary agglutination reagent:agglutinable particle complex wherein said second primary agglutination reagent is capable of binding to said second epitope; and (d) forming a second mixture by mixing said first mixture and said agent wherein agglutination in the second mixture indicates the presence of the analyte in the sample.

23. The assay of claim 21 wherein the agglutinable particles of the primary agglutination agent are selected from the group consisting of latex, charcoal, kaolinite, bentonite, microbial cells and red blood cells.

24. The assay of claim 21 wherein said sample is selected from the group consisting of whole blood, a separated blood fraction, urine, semen, saliva, cerebrospinal fluid, amniotic fluid, ascites fluid, pleural effusion, cyst fluid, pus and tissue extracts.

25. A two site direct agglutination assay for the detection of the simultaneous presence of two different analytes in a sample wherein the first and second analytes each comprise at least one analyte-binding site, the assay comprising:

(a) providing a first primary agglutination reagent which is capable of binding simultaneously to an agglutinable particle and to said first analyte;

(b) providing agglutinable particles to which said first primary agglutination reagent can bind, if such particles are not already present in the sample;

(c) forming a first mixture of a first sample portion, said first agglutination reagent, and bindable agglutinable particles to obtain first analyte:first agglutination reagent:particle complex;

(d) providing a primary agglutination agent comprising a second primary agglutination reagent:particle complex wherein said second primary agglutination reagent is capable of binding to said second analyte thereby forming a second complex;

(e) providing a secondary agglutination reagent which can bind simultaneously to both said first complex and to said second complex, in each case being specific for a native epitope of the analyte or an epitope formed by the binding of the primary reagent to said analyte, but not able to bind to two complexes of the same analyte;

(f) forming a second mixture of said first mixture, said primary agglutination agent and said secondary agglutination reagents, wherein agglutination of said second mixture indicates the simultaneous presence of said first and second analytes in the sample.

26. A two site direct agglutination assay for the detection of the simultaneous presence of two different analytes in a sample wherein the first and second analytes each comprise at least one analyte-binding site, the assay comprising:

(a) providing a first primary agglutination agent comprising a first primary agglutination reagent:particle complex wherein said first primary agglutination reagent is capable of binding to said first analyte thereby forming a first complex;

(b) providing a second primary agglutination agent comprising a second primary agglutination reagent:particle complex wherein said second primary agglutination reagent is capable of binding to said second analyte thereby forming a second complex;

(e) providing a secondary agglutination reagent which can bind simultaneously to both said first complex and to said second complex, in each case being specific for a native epitope of the analyte or an epitope formed by the binding of the primary reagent to said analyte, but not able to bind to two complexes of the same analyte;

(f) forming a first mixture of said sample, said first and second primary agglutination agents and said secondary agglutination reagents, wherein agglutination of said first mixture indicates the simultaneous presence of said first and second analytes in the sample.

27. A two site direct agglutination assay for the detection of the simultaneous presence of three different analytes in a sample wherein each of said analytes comprises at least one analyte binding site, the assay comprising:

(a) providing a first primary agglutination reagent which is capable of binding simultaneously to a first agglutinable particle and to a first analyte;

(b) providing a second primary agglutination reagent which is capable of binding simultaneously to a second agglutinable particle and to a second analyte;

(c) providing first and second agglutinable particles to which said first and second primary agglutination reagents can bind respectively, if such particles are not already present in said sample;

(d) forming a first mixture of a first portion of the sample, said first primary agglutination reagent and said first agglutinable particles to obtain a first analyte:first primary agglutination reagent:first particle complex;

(e) forming a second mixture of a second portion of the sample, said second primary agglutination reagent and said second agglutinable particles to obtain a second analyte:second primary agglutination reagent:second particle complex;

(f) providing first and second secondary agglutination reagents wherein said first secondary agglutination reagents can bind simultaneously to both said first complex and to a third analyte, said third analyte having at least two epitopes, and said secondary agglutination reagent can bind simultaneously to both said second complex and to said third analyte;

(g) forming a third mixture of the first mixtures the second mixture and the first and second secondary agglutination reagents, wherein agglutination of said third mixture indicates the simultaneous presence of said first second and third analytes in the sample.

28. An assay for an allergen-specific IgE antibody in whole blood comprising:

(a) providing a heterobispecific anti-erythrocyte and anti-IgE antibody specific for the IgE of the species from which said whole blood is obtained, said heterobispecific antibody being capable of binding to only one site on the IgE molecule;

(b) providing a known quantity of a multivalent allergen bound by said IgE antibody;

(c) reacting the whole blood sample with said heterobispecific antibody and said allergen, whereby erythrocytes endogenous to said whole blood sample are agglutinated if and only if an IgE antibody which binds said allergen multivalently is present.

29. An assay for an allergen-specific IgM antibody in whole blood comprising:

(a) providing a heterobispecific anti-erythrocyte and anti-IgM antibody specific for the IgM of the species from which said whole blood is obtained, said heterobispecific antibody being capable of binding to only one site on the IgM molecule;

(b) providing a known quantity of a multivalent allergen bound by said IgM antibody;

(c) reacting the whole blood sample with said heterobispecific antibody and said allergen whereby erythrocytes endogenous to said whole blood sample are agglutinated if and only if an IgM antibody which binds said allergen multivalently is present.

30. The assay of claim 1 wherein an amount effective to cause detectable agglutination of the agglutinable particles are native to the sample; and said native particles are red blood cells.

31. The assay of claim 1 wherein an amount effective to cause detectable agglutination of the agglutinable particles are added to the sample; and said added particles are latex particles.

32. The assay of claim 1 in which the first and second reagents are heterobispecific antibodies.

33. The assay of claim 1 in which the first and second reagents bind identical epitopes of said particle.

34. The assay of claim 1 wherein, in steps (b) and (c), essentially all of the excess reagent is particle bound.

35. The assay of claim 1, wherein the sensitivity of the assay is higher than that obtained in a reference assay in which both reagents are added directly to the entire sample rather than individually to said first and second sample portions.

36. The assay of claim 35 wherein the amount of analyte in the sample is such that with the amounts of reagents and sample employed, there would be no detectable agglutination in said reference assay, but there is detectable agglutination in the claimed assay.

37. An assay for the detection of an analyte in a sample, wherein the analyte includes a first nonrepeating epitope and a second nonrepeating epitope, the assay comprising:

(a) providing first and second primary agglutination reagents, each of which is capable of binding simultaneously to an agglutinable particle, and to a nonrepeating epitope of said analyte, said first and second reagents binding to different, non-overlapping, nonrepeating epitopes of said analyte;

(b) forming a first mixture of a first sample portion, an excess of said first reagent relative to said analyte, and agglutinable particles bindable by said first reagent;

(c) forming a second mixture of a second sample portion, an excess of said second reagent relative to said analyte, and agglutinable particles bindable by said second reagent; and (d) forming a third mixture by mixing said first and second mixtures, wherein, in steps (b) and (c), essentially all of the excess reagent is particle bound, and wherein agglutination in the third mixture indicates the presence of the analyte in the sample.

38. An assay for the detection of an analyte in a sample, wherein the analyte includes a first nonrepeating epitope and a second nonrepeating epitope, the assay comprising:

(a) providing first and second primary agglutination reagents, each of which is capable of binding simultaneously to an agglutinable particle, and to a nonrepeating epitope of said analyte, said first and second reagents binding to different, non-overlapping, nonrepeating epitopes of said analyte;

(b) forming a first mixture of a first sample portion, an excess of said first reagent relative to said analyte, and agglutinable particles bindable by said first reagent;

(c) forming a second mixture of a second sample portion, an excess of said second reagent relative to said analyte, and agglutinable particles bindable by said second reagent; and (d) forming a third mixture by mixing said first and second mixtures, wherein the sensitivity of the assay is higher than that obtained in a reference assay in which both reagents were added directly to the entire sample rather than individually to said first and second sample portions, and wherein agglutination in the third mixture indicates the presence of the analyte in the sample.

* * * * *